(12) United States Patent
Green et al.

(10) Patent No.: US 7,866,526 B2
(45) Date of Patent: Jan. 11, 2011

(54) APPARATUS FOR APPLYING SURGICAL FASTENERS TO BODY TISSUE

(75) Inventors: David T Green, Fairfield, CT (US);
Henry Bolanos, Norwalk, CT (US);
Wayne Young, Brewster, NY (US);
Stephan A DeFonzo, Wayne, PA (US);
Richard A McGarry, Norwalk, CT (US); Dominick L Mastri, Bridgeport, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 12/548,053

(22) Filed: Aug. 26, 2009

(65) Prior Publication Data

US 2009/0308908 A1 Dec. 17, 2009

Related U.S. Application Data

(60) Division of application No. 11/978,852, filed on Oct. 30, 2007, now Pat. No. 7,681,772, which is a continuation of application No. 10/753,248, filed on Jan. 8, 2004, now Pat. No. 7,624,903, which is a continuation of application No. 09/957,620, filed on Sep. 20, 2001, now abandoned, which is a continuation of application No. 08/959,644, filed on Oct. 28, 1997, now abandoned, which is a continuation of application No. 08/714,911, filed on Sep. 17, 1996, now abandoned, which is a continuation of application No. 08/540,728, filed on Oct. 11, 1995, now abandoned, which is a continuation of application No. 08/318,585, filed on Oct. 5, 1994, now abandoned, which is a continuation of application No. 07/861,065, filed on Mar. 31, 1992, now Pat. No. 5,364,002, which is a continuation-in-part of application No. 07/782,290, filed on Oct. 18, 1991, now Pat. No. 5,289,963.

(51) Int. Cl.
*A61B 17/068* (2006.01)
(52) U.S. Cl. .................. 227/175.1; 227/19; 227/176.1; 227/179.1
(58) Field of Classification Search .............. 227/175.1, 227/19, 176.1, 179.1
See application file for complete search history.

(56) References Cited

U.S. PATENT DOCUMENTS 389,660 A 9/1888 Mandel et al.

(Continued)

FOREIGN PATENT DOCUMENTS

DE 2330182 1/1975

(Continued)

OTHER PUBLICATIONS

Article, Swain, C.P., Mills, T.N. "An Endoscopic Sewing Machine", Gastro-intestinal Endoscopy; 1986, vol. 32, No. 1, pp. 36-38.

(Continued)

*Primary Examiner*—Brian D Nash

(57) ABSTRACT

An apparatus for endoscopic application of surgical staples adapted to attach surgical mesh to body tissue includes a frame and an elongated endoscopic section connected to the frame and extending distally therefrom. A staple storage cartridge is removably supported on a pivotal support system at the distal end portion of the endoscopic section. An elongated pusher system is provided for individually advancing at least one staple at a time distally. The pusher system includes a trigger system to actuate the pusher. The trigger system is provided with perceptible tactile sensing means to indicate when the legs of the staple being advanced are exposed so as to be visible to the user for positioning and orientation purposes.

8 Claims, 21 Drawing Sheets

U.S. PATENT DOCUMENTS

| | | |
|---|---|---|
| 2,448,741 A | 9/1948 | Scott et al. |
| 3,054,406 A | 9/1962 | Usher |
| 3,124,136 A | 3/1964 | Usher |
| 3,314,431 A | 4/1967 | Smith, Jr. |
| 3,494,533 A | 2/1970 | Green et al. |
| 3,593,903 A | 7/1971 | Astafiev et al. |
| 3,610,231 A * | 10/1971 | Takahashi et al. ........... 600/139 |
| 3,643,851 A | 2/1972 | Green et al. |
| 3,763,860 A | 10/1973 | Clarke |
| 3,777,538 A | 12/1973 | Weatherly et al. |
| 3,788,303 A * | 1/1974 | Hall ........................... 600/148 |
| 3,837,555 A | 9/1974 | Green |
| 3,871,379 A | 3/1975 | Clarke |
| 3,892,228 A | 7/1975 | Mitsui |
| 3,955,581 A | 5/1976 | Spasiano et al. |
| RE28,932 E | 8/1976 | Noiles et al. |
| 4,014,492 A | 3/1977 | Rothfuss |
| 4,027,510 A | 6/1977 | Hiltebrandt |
| 4,043,504 A | 8/1977 | Hueil et al. |
| 4,127,227 A | 11/1978 | Green |
| 4,196,836 A | 4/1980 | Becht |
| 4,203,430 A * | 5/1980 | Takahashi ................... 600/149 |
| 4,204,623 A | 5/1980 | Green |
| 4,207,873 A | 6/1980 | Kruy |
| 4,256,251 A | 3/1981 | Moshofsky |
| 4,261,244 A | 4/1981 | Becht et al. |
| 4,294,233 A * | 10/1981 | Takahashi ................... 600/149 |
| 4,296,751 A | 10/1981 | Blake, III et al. |
| 4,316,468 A | 2/1982 | Klieman et al. |
| 4,317,535 A | 3/1982 | Huftel et al. |
| 4,321,002 A | 3/1982 | Froehlich |
| 4,347,847 A | 9/1982 | Usher |
| 4,349,028 A | 9/1982 | Green |
| 4,375,866 A | 3/1983 | Giersch et al. |
| 4,391,402 A | 7/1983 | Campbell et al. |
| 4,399,810 A | 8/1983 | Samuels et al. |
| 4,403,693 A | 9/1983 | Froehlich |
| 4,406,392 A | 9/1983 | Campbell et al. |
| 4,407,286 A | 10/1983 | Noiles et al. |
| 4,452,245 A | 6/1984 | Usher |
| 4,454,875 A | 6/1984 | Pratt et al. |
| 4,470,532 A | 9/1984 | Froehlich |
| 4,485,816 A | 12/1984 | Krumme |
| 4,485,953 A | 12/1984 | Rothfuss |
| 4,489,875 A | 12/1984 | Crawford et al. |
| 4,496,090 A | 1/1985 | Crevier et al. |
| 4,505,273 A | 3/1985 | Braun et al. |
| 4,506,819 A | 3/1985 | Rand |
| 4,509,518 A | 4/1985 | McGarry et al. |
| 4,519,532 A | 5/1985 | Foslien |
| 4,520,817 A | 6/1985 | Green |
| 4,523,695 A | 6/1985 | Braun et al. |
| 4,523,707 A | 6/1985 | Blake, III et al. |
| 4,526,174 A | 7/1985 | Froehlich |
| 4,527,724 A | 7/1985 | Chow et al. |
| 4,527,726 A | 7/1985 | Assell et al. |
| 4,532,927 A | 8/1985 | Miksza, Jr. |
| 4,550,715 A | 11/1985 | Santangelo et al. |
| 4,562,839 A | 1/1986 | Blake, III et al. |
| 4,566,620 A | 1/1986 | Green |
| 4,573,622 A | 3/1986 | Green et al. |
| 4,583,670 A | 4/1986 | Alvarado |
| 4,591,086 A | 5/1986 | Campbell et al. |
| 4,592,498 A | 6/1986 | Braun et al. |
| 4,596,350 A | 6/1986 | Smith et al. |
| 4,603,693 A | 8/1986 | Conta et al. |
| 4,607,638 A | 8/1986 | Crainich |
| 4,610,251 A | 9/1986 | Kumar |
| 4,610,383 A | 9/1986 | Rothfuss et al. |
| 4,616,650 A | 10/1986 | Green et al. |
| 4,618,086 A | 10/1986 | Li et al. |
| 4,619,391 A | 10/1986 | Sharkany et al. |
| 4,624,254 A | 11/1986 | McGarry et al. |
| 4,634,035 A | 1/1987 | Li et al. |
| 4,655,221 A | 4/1987 | Devereux |
| 4,662,373 A | 5/1987 | Montgomery et al. |
| 4,662,555 A | 5/1987 | Thornton |
| 4,664,305 A | 5/1987 | Blake, III et al. |
| 4,665,906 A | 5/1987 | Jervis |
| 4,671,279 A | 6/1987 | Hill |
| 4,688,555 A | 8/1987 | Wardle |
| 4,691,853 A | 9/1987 | Storace |
| 4,706,655 A | 11/1987 | Krauter |
| 4,706,668 A | 11/1987 | Backer |
| 4,719,917 A | 1/1988 | Barrows et al. |
| 4,728,020 A | 3/1988 | Green et al. |
| 4,747,531 A | 5/1988 | Brinkerhoff et al. |
| 4,763,669 A | 8/1988 | Jaeger |
| 4,784,137 A | 11/1988 | Kulik et al. |
| 4,787,387 A | 11/1988 | Burbank, III et al. |
| 4,789,090 A | 12/1988 | Blake, III |
| 4,802,478 A | 2/1989 | Powell |
| 4,807,628 A | 2/1989 | Peters et al. |
| 4,811,886 A | 3/1989 | Murray |
| 4,821,939 A | 4/1989 | Green |
| 4,821,942 A | 4/1989 | Richards et al. |
| 4,838,884 A | 6/1989 | Dumican et al. |
| 4,841,888 A | 6/1989 | Mills et al. |
| 4,872,456 A | 10/1989 | Hasson |
| 4,874,122 A | 10/1989 | Froelich et al. |
| 4,880,015 A | 11/1989 | Nierman |
| 4,887,601 A | 12/1989 | Richards |
| 4,887,756 A | 12/1989 | Puchy |
| 4,899,745 A | 2/1990 | Laboureau et al. |
| 4,919,112 A | 4/1990 | Siegmund |
| 4,919,152 A | 4/1990 | Ger |
| 4,919,320 A | 4/1990 | Storace |
| 4,934,364 A | 6/1990 | Green |
| 4,944,443 A | 7/1990 | Oddsen et al. |
| 4,951,861 A | 8/1990 | Schulze et al. |
| RE33,362 E | 10/1990 | Mongeon et al. |
| 4,978,049 A | 12/1990 | Green |
| 4,997,436 A | 3/1991 | Oberlander |
| 5,002,551 A | 3/1991 | Linsky et al. |
| 5,015,249 A | 5/1991 | Nakao et al. |
| 5,040,715 A | 8/1991 | Green et al. |
| 5,042,707 A | 8/1991 | Taheri |
| 5,047,038 A | 9/1991 | Peters et al. |
| 5,049,152 A | 9/1991 | Simon et al. |
| 5,049,153 A | 9/1991 | Nakao et al. |
| 5,053,038 A | 10/1991 | Sheehan |
| 5,071,430 A | 12/1991 | de Salis et al. |
| 5,084,057 A | 1/1992 | Green et al. |
| 5,100,420 A | 3/1992 | Green et al. |
| 5,125,553 A | 6/1992 | Oddsen et al. |
| 5,147,373 A | 9/1992 | Ferzli |
| 5,156,609 A | 10/1992 | Nakao |
| 5,161,725 A | 11/1992 | Murray et al. |
| 5,163,945 A | 11/1992 | Ortiz et al. |
| 5,174,487 A | 12/1992 | Rothfuss et al. |
| 5,176,702 A | 1/1993 | Bales et al. |
| 5,220,928 A | 6/1993 | Oddsen et al. |
| 5,222,975 A | 6/1993 | Crainich |
| 5,240,163 A | 8/1993 | Stein et al. |
| 5,246,156 A | 9/1993 | Rothfuss et al. |
| 5,246,450 A | 9/1993 | Thornton et al. |
| 5,251,801 A | 10/1993 | Ruckdeschel et al. |
| 5,289,963 A | 3/1994 | McGarry et al. |
| 5,307,976 A | 5/1994 | Olson et al. |
| 5,312,023 A | 5/1994 | Green et al. |
| 5,318,221 A | 6/1994 | Green et al. |
| 5,381,943 A | 1/1995 | Allen et al. |
| 5,397,324 A | 3/1995 | Carroll et al. |
| 5,452,836 A * | 9/1995 | Huitema et al. ........... 227/176.1 |

| | | |
|---|---|---|
| 5,484,095 A | 1/1996 | Green et al. |
| 5,484,451 A | 1/1996 | Akopov et al. |
| 5,547,117 A * | 8/1996 | Hamblin et al. .......... 227/175.2 |
| 5,632,432 A * | 5/1997 | Schulze et al. ........... 227/176.1 |
| 5,636,780 A | 6/1997 | Green et al. |
| 5,690,269 A | 11/1997 | Bolanos et al. |
| 5,752,644 A * | 5/1998 | Bolanos et al. .......... 227/180.1 |
| 5,797,538 A | 8/1998 | Heaton et al. |
| 5,797,959 A * | 8/1998 | Castro et al. ................ 606/207 |
| 5,901,895 A | 5/1999 | Heaton et al. |

FOREIGN PATENT DOCUMENTS

| | | |
|---|---|---|
| DE | 2703529 | 8/1978 |
| DE | 3301713 | 7/1984 |
| EP | 0041022 | 12/1981 |
| EP | 116220 | 8/1984 |
| EP | 0484677 | 5/1992 |
| EP | 0085930 | 8/1993 |
| FR | 1164133 | 10/1958 |
| FR | 1169438 | 12/1958 |
| WO | WO 93/14706 | 8/1993 |

PUBLICATIONS

Article, Swain, C.P., Brown, G.J. and Mills, T.N. "An Endoscopic Stapling Device: The Development of a New Flexible Endoscopically Controlled Device for Placing Multiple Transmural Staples in Gastrointestinal Tissue", Gastrointestinal Endoscopy, 1989, vol. 35, No. 4, pp. 338-339.

Publication Entitled "A Quick Stapler Tie-Over Fixation for Skin Grafts", by Haim Y. Kaplan, M.D., Ann. Plast. Surg., 22:173,1989, pp. 173-174.

Publication Entitled "A Rapid and Effective Method of Skin Graft Stabilization in Burned Children", by J.B.Boyd et al., The Hospital for Sick Children, Toronto, Canada, 1982, pp. 400-401.

Publication Entitled "A Simple Bolster Technique for Skin Grafting", by Henry T. Hoffman, M.D. and Michael LaRouere, M.D., Department of Otolaryngology, University of Michigan, Laryngoscope 99, May 1989, p. 558.

M-D-D-I Report, Sep. 1991 Ethicon Endoscopic Staple for Hernia Repair.

Information Booklet for Auto Suture ôSkin & Fascia Suture ôSurgical Stapling Instruments, Instruments Corp.

Information Booklet for Auto Suture ôMultifire Premium ä Disposable Skin Stapler and Disposable Loading Unit.

Publication Entitled Shape Memory Alloys From Scientific American Nov. 1979.

* cited by examiner

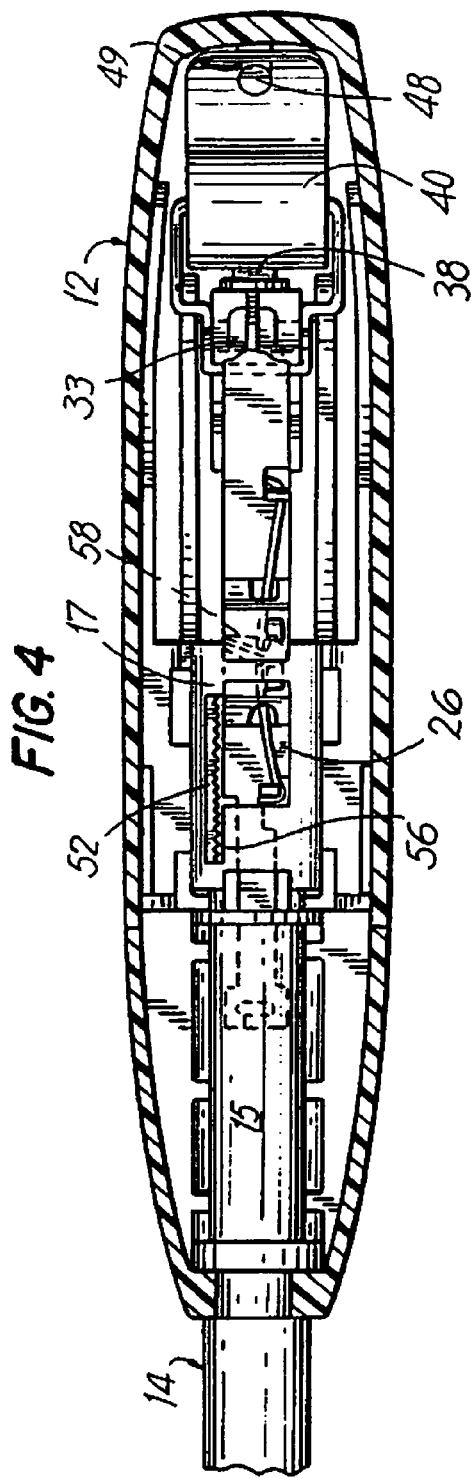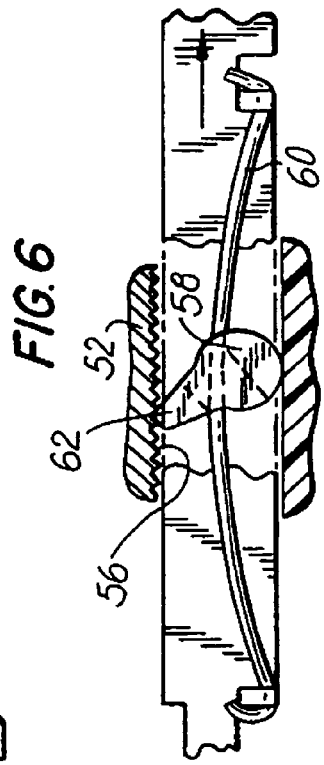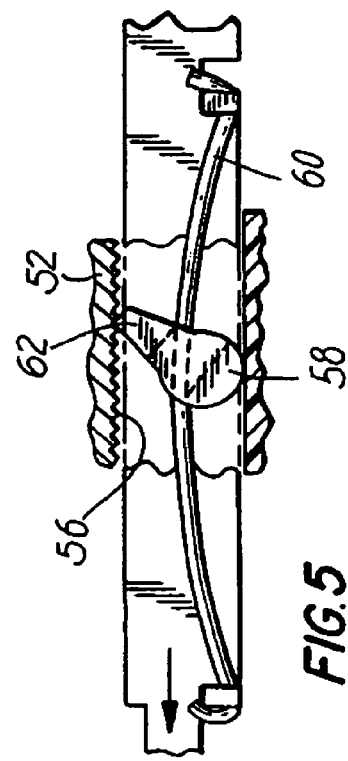

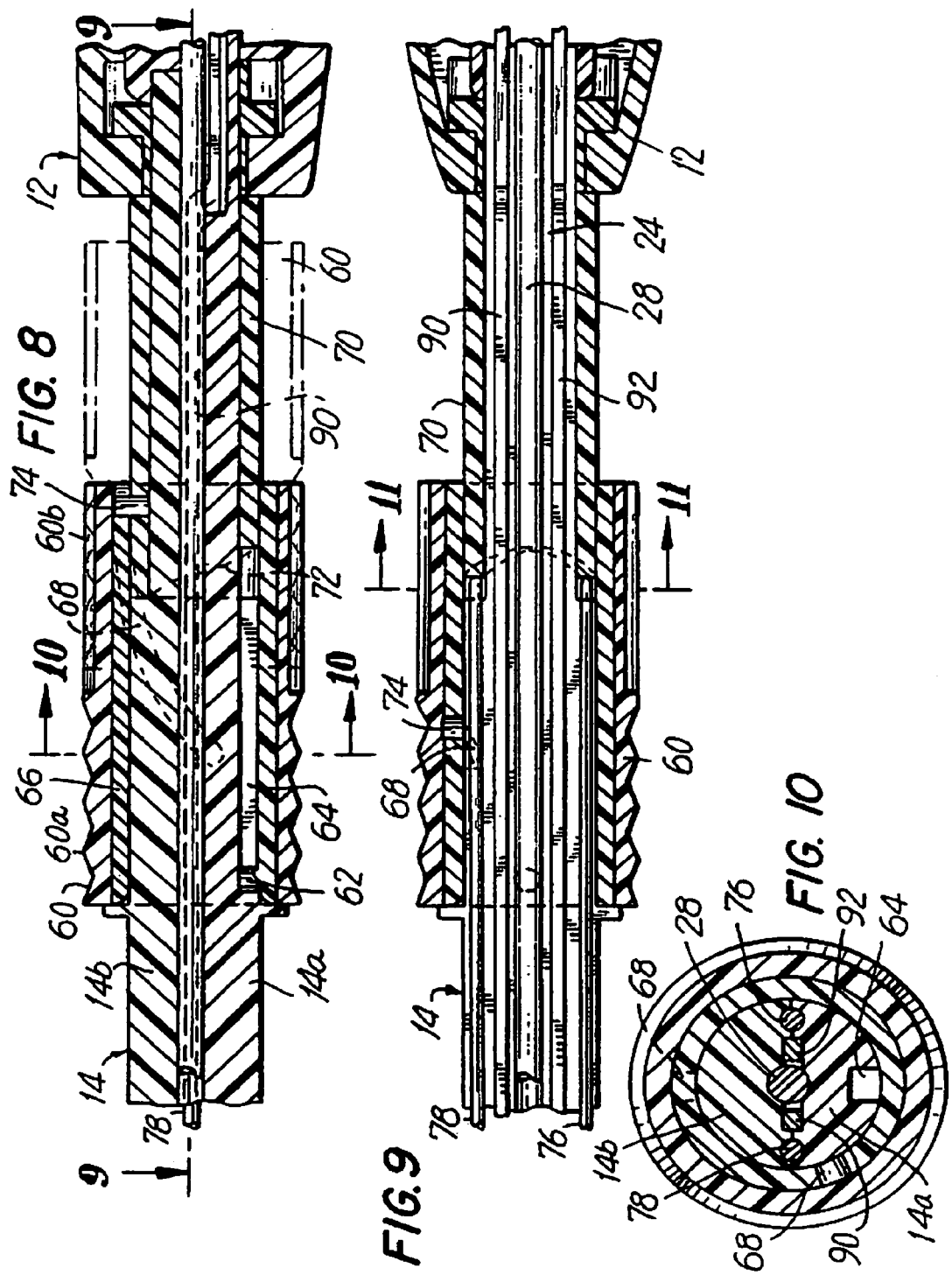

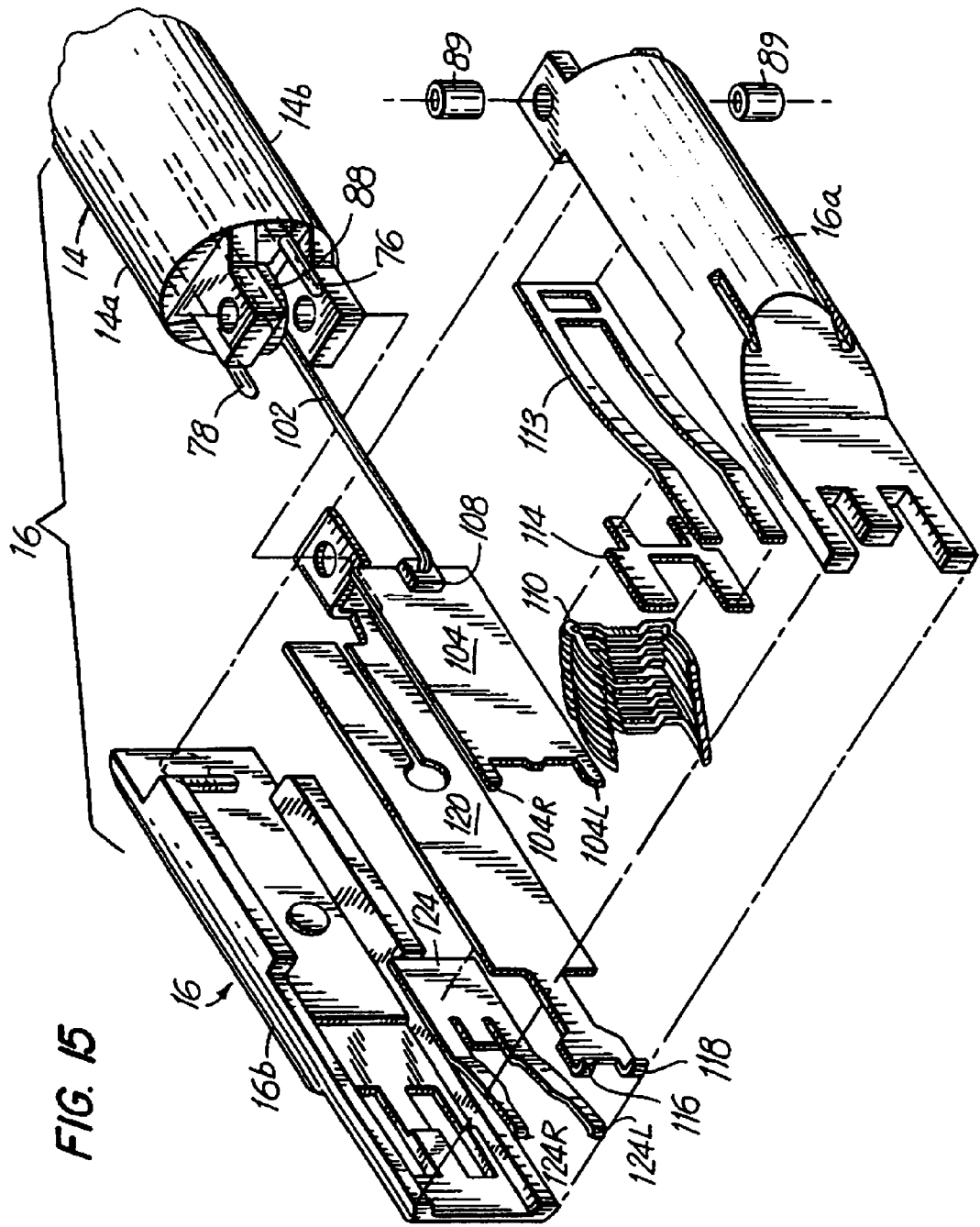

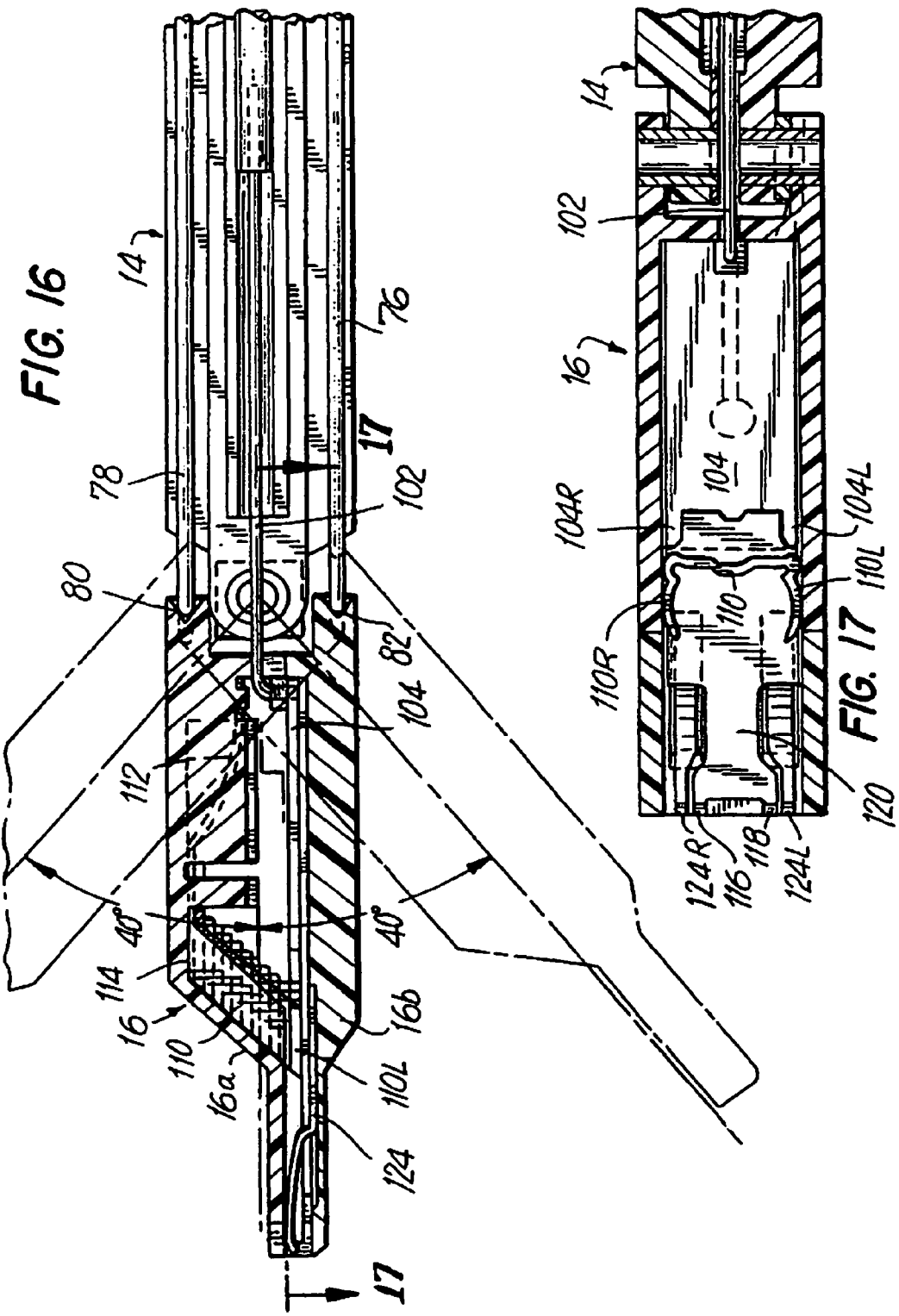

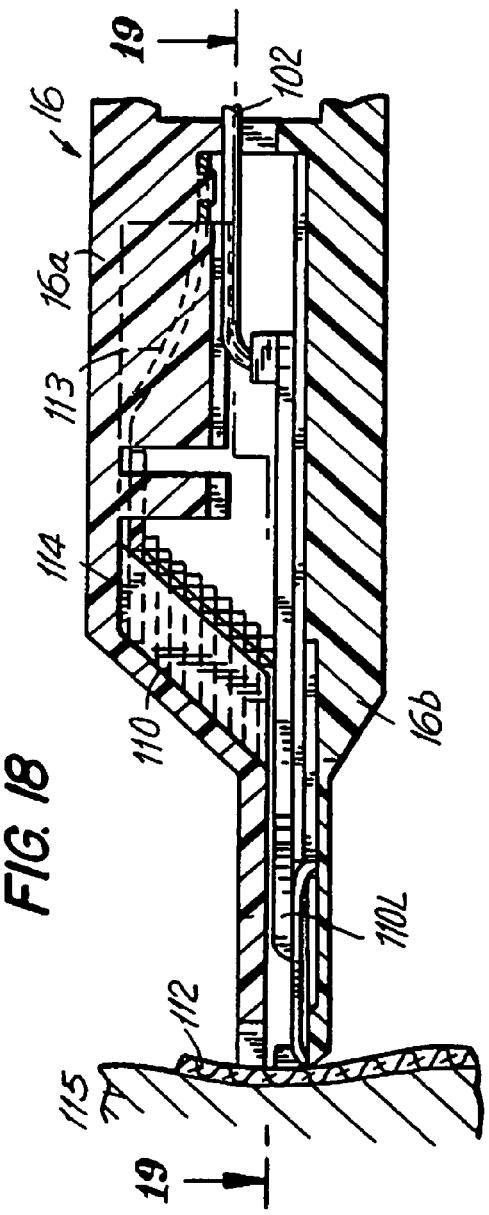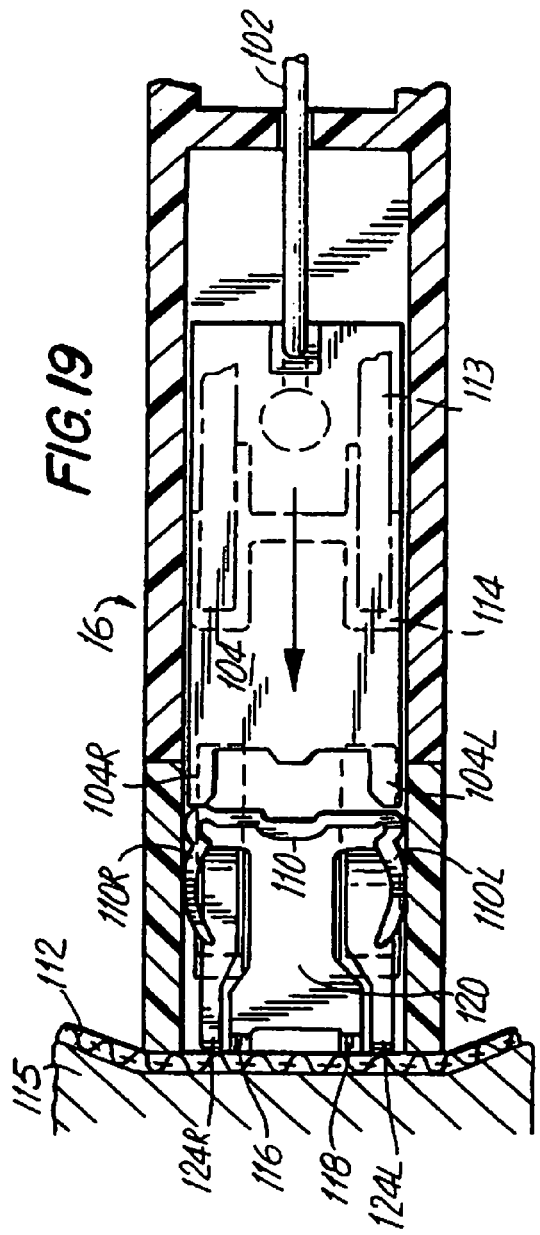

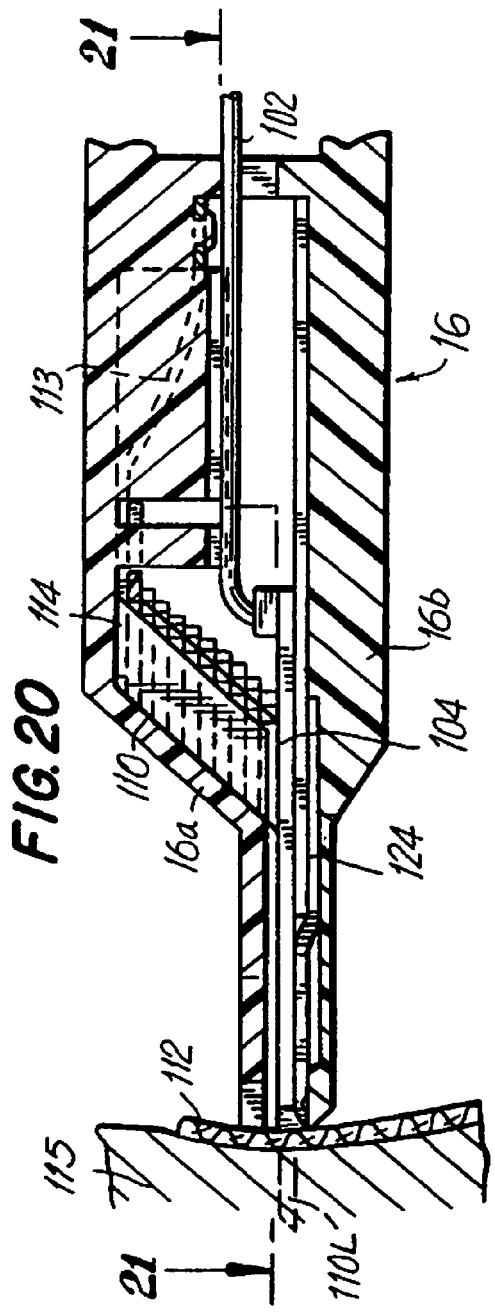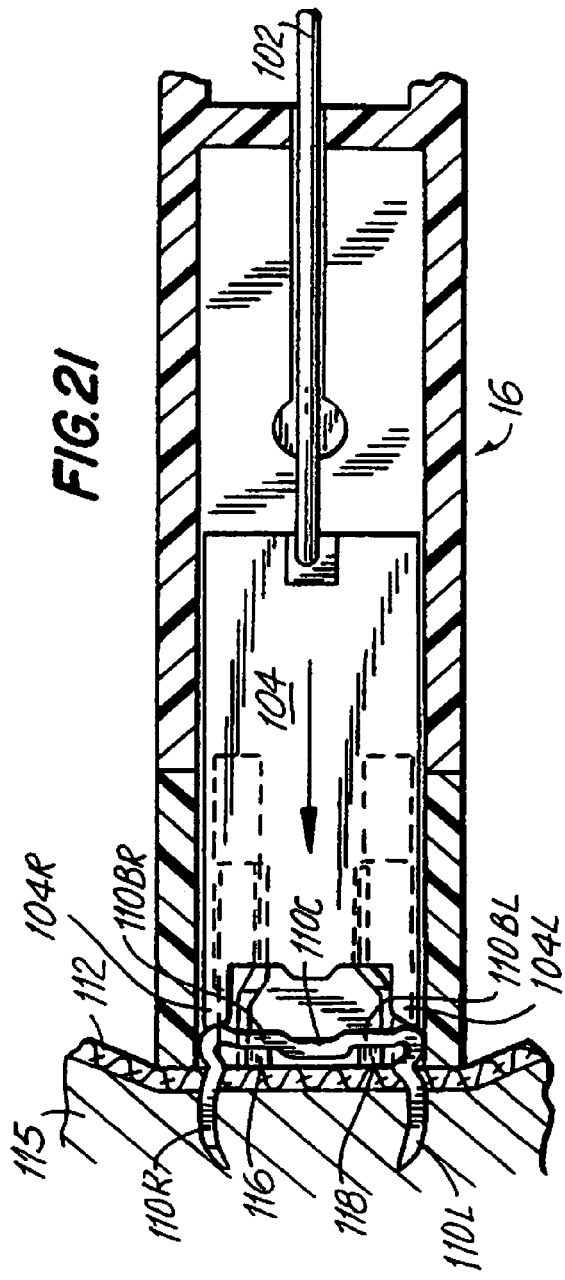

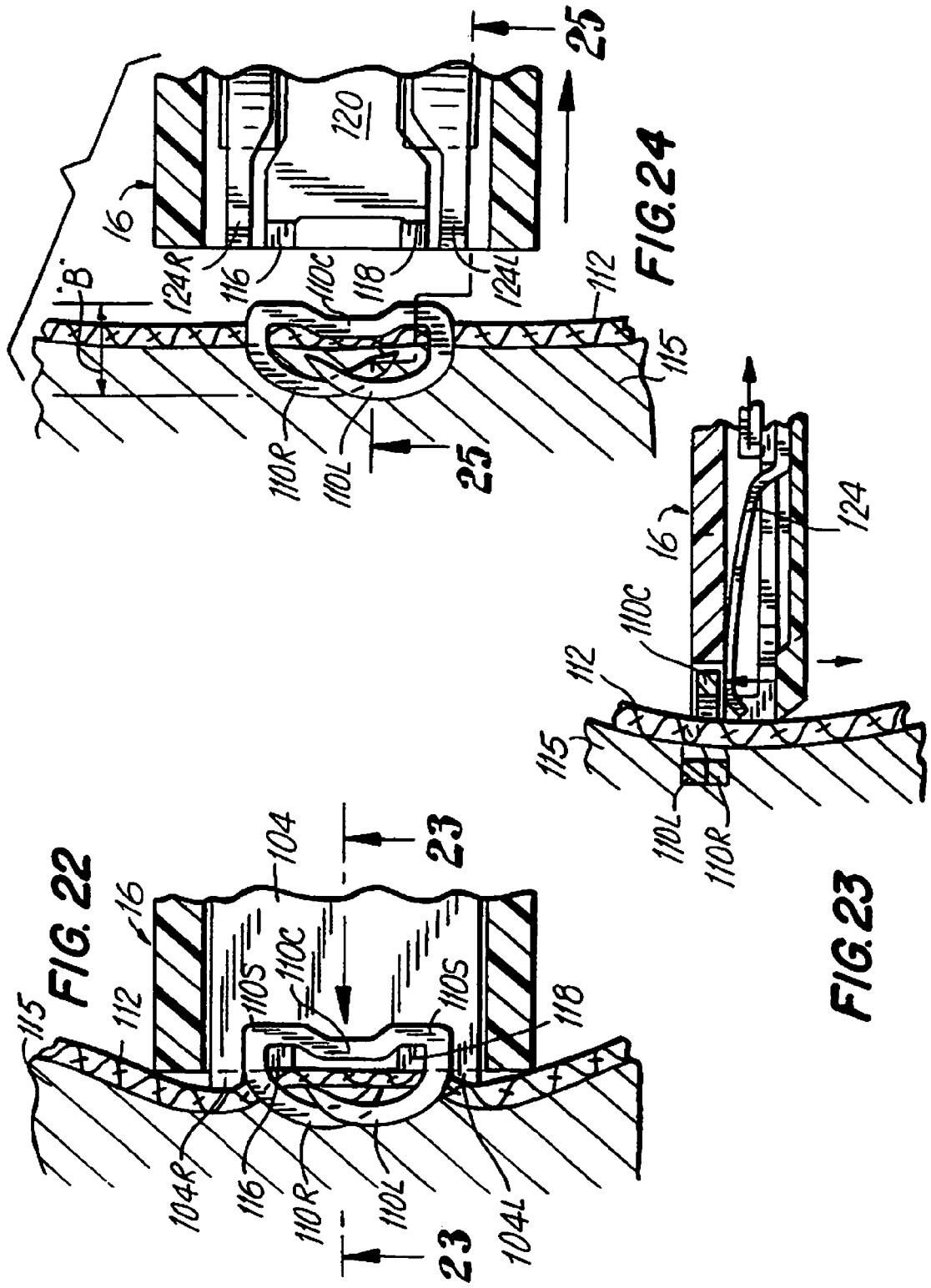

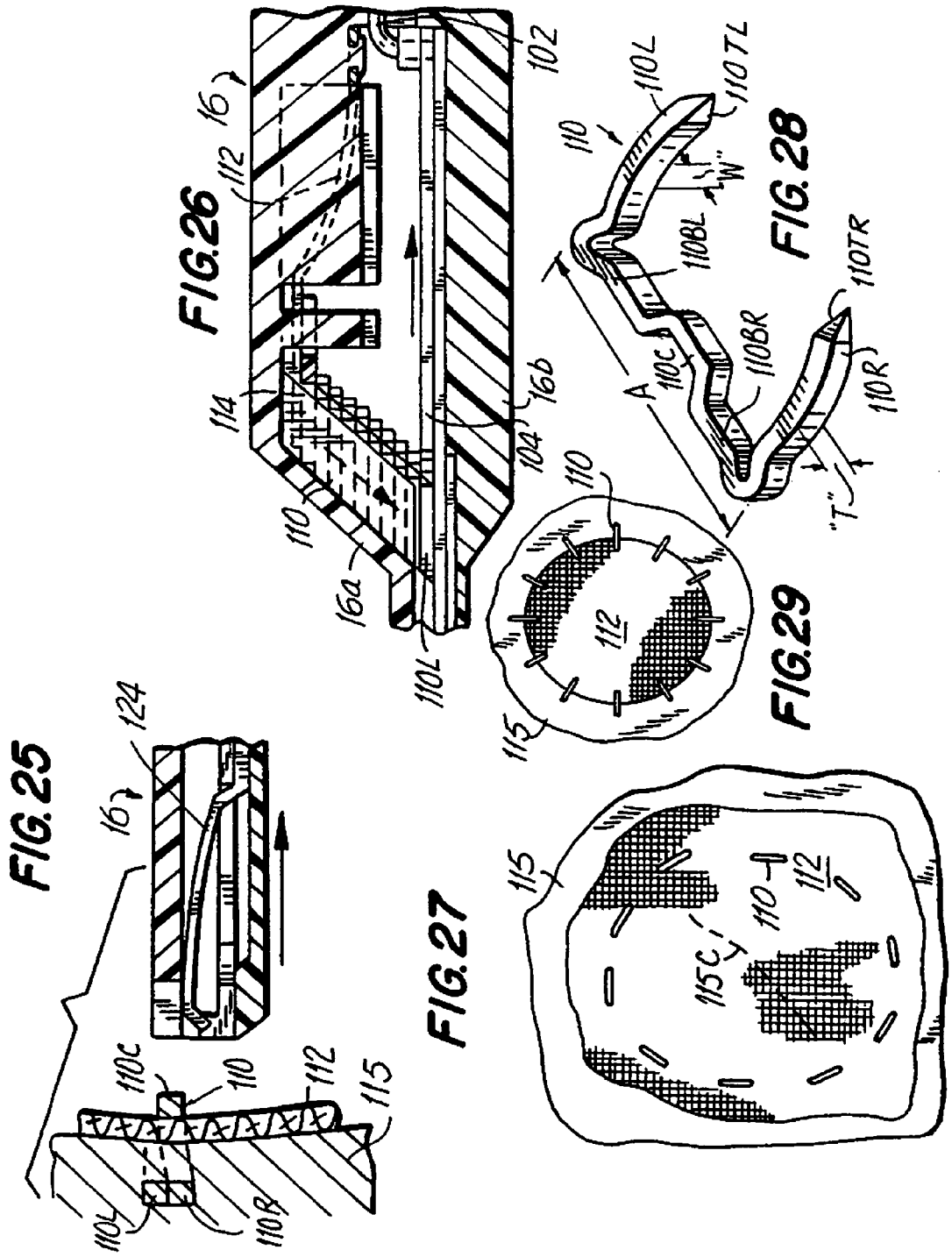

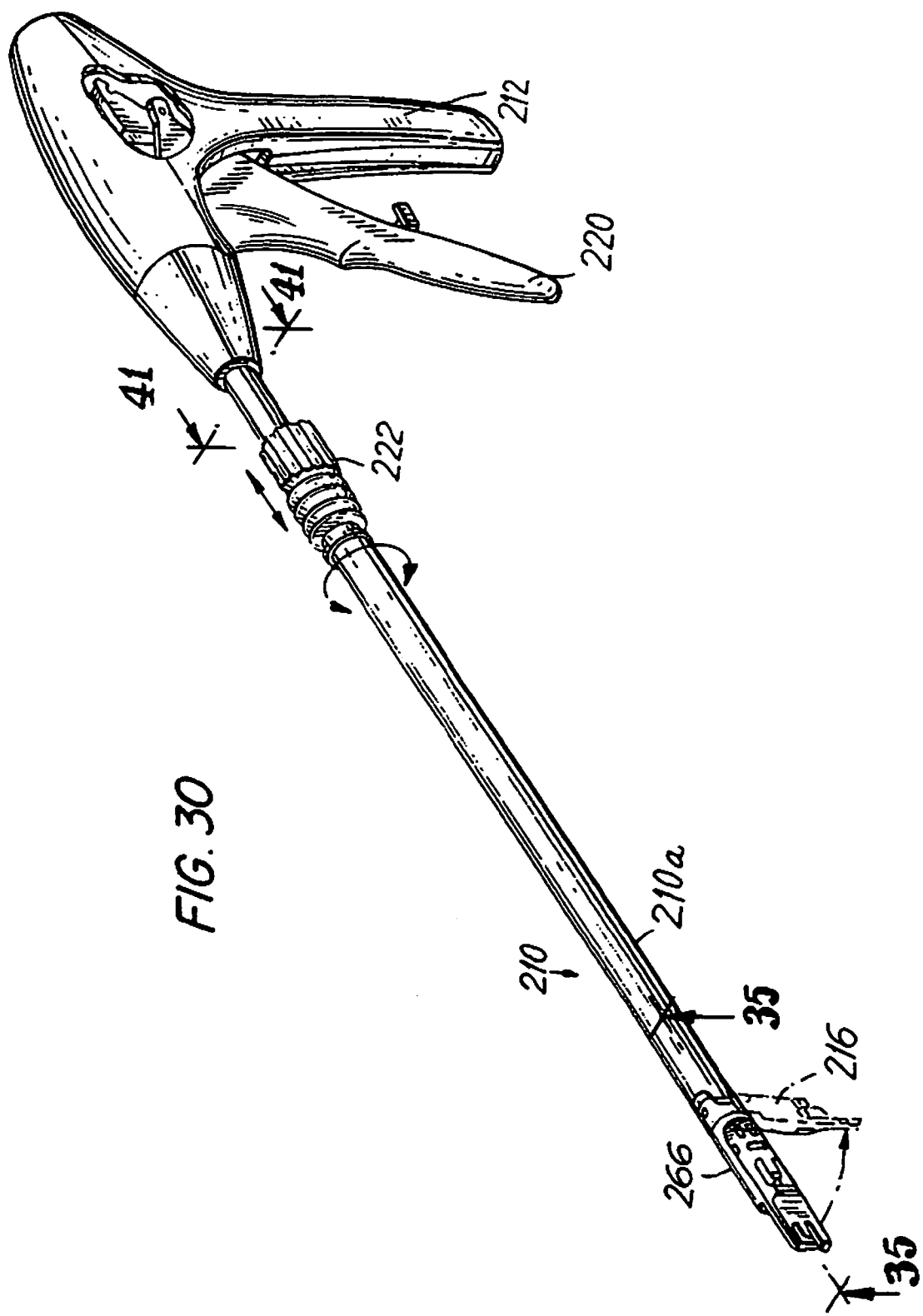

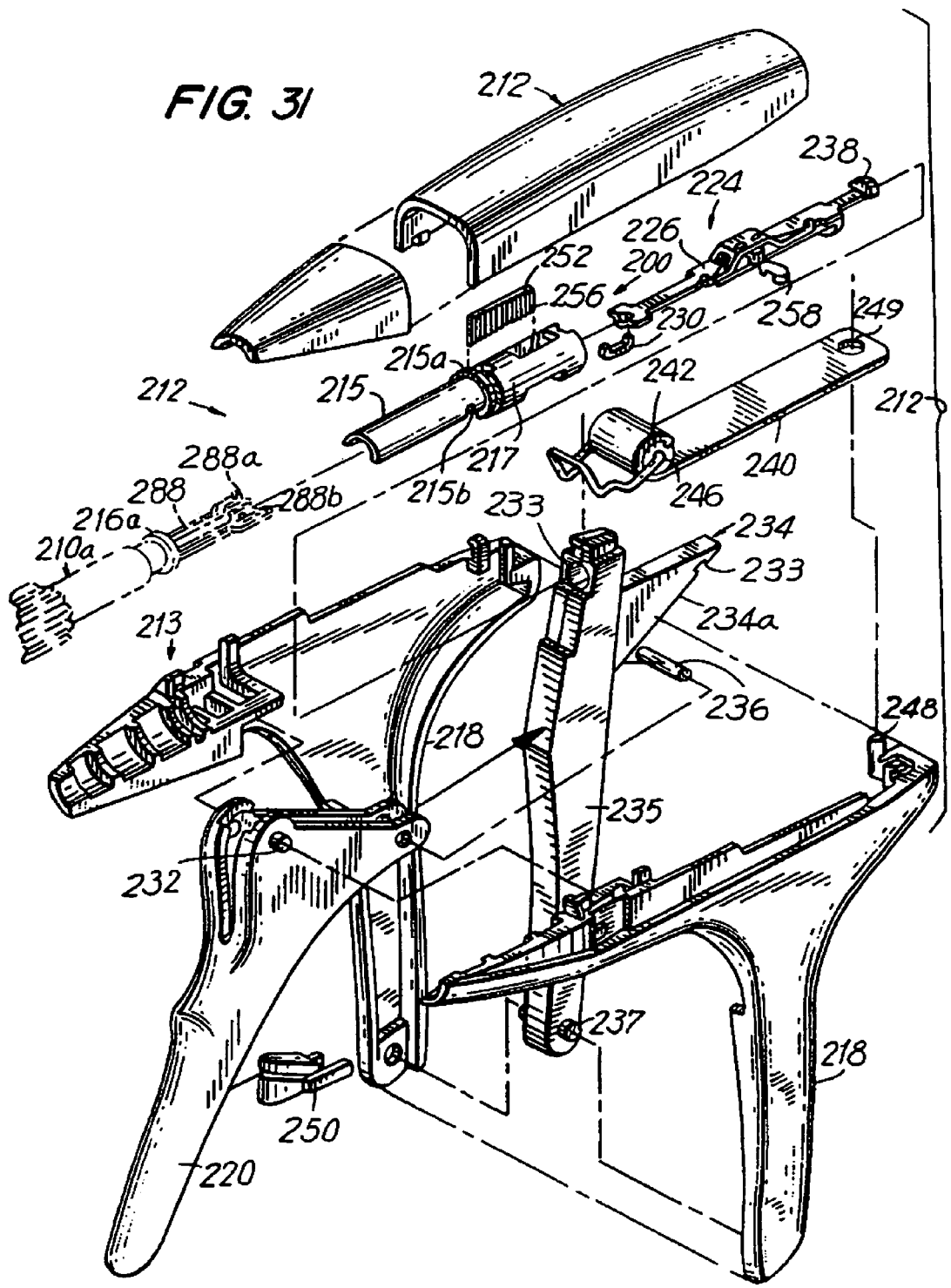

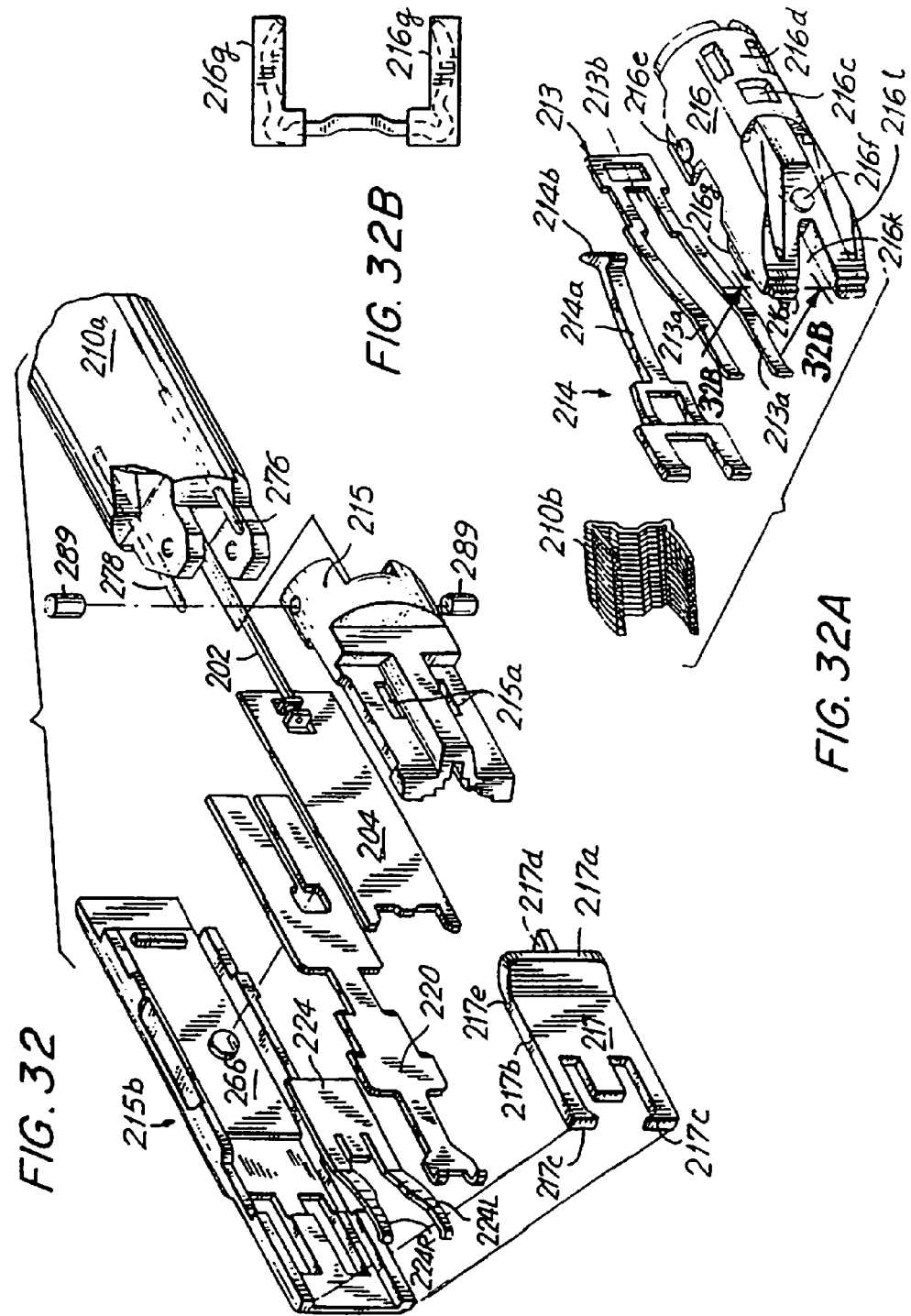

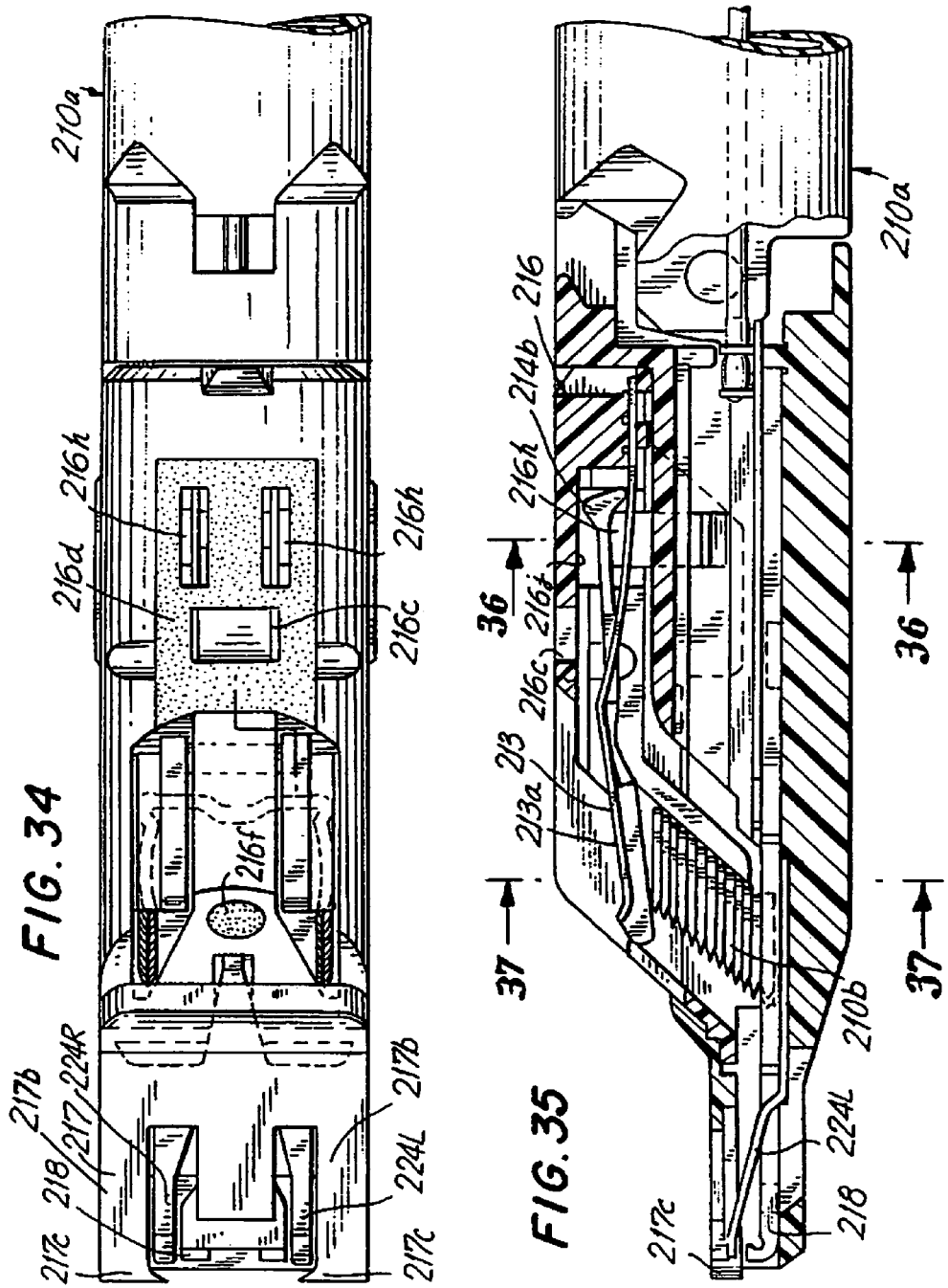

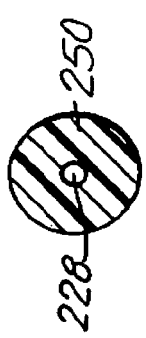
FIG.41
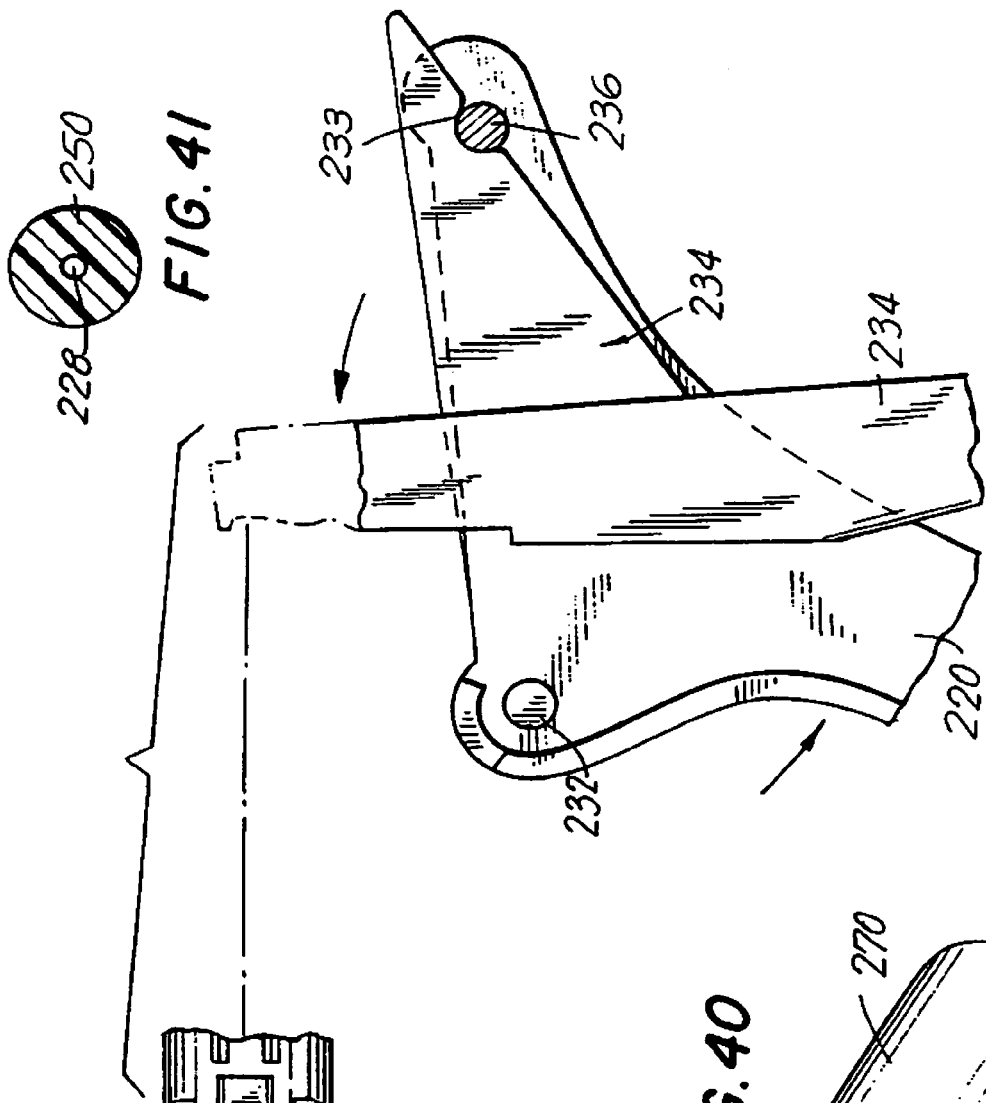
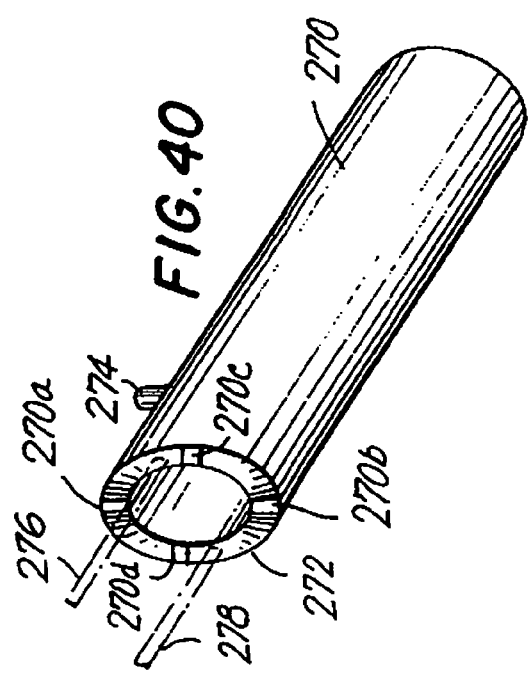
FIG.39
FIG.40

APPARATUS FOR APPLYING SURGICAL FASTENERS TO BODY TISSUE

CROSS-REFERENCE TO RELATED APPLICATIONS

This application is a division of U.S. patent application Ser. No. 11/978,852, filed on Oct. 30, 2007, now U.S. Pat. No. 7,681,772, which is a continuation of U.S. patent application Ser. No. 10/753,248, filed on Jan. 8, 2004, now U.S. Pat. No. 7,624,903, which is a continuation of U.S. patent application Ser. No. 09/957,620, filed Sep. 20, 2001, now abandoned, which is a continuation of U.S. patent application Ser. No. 08/959,644, filed on Oct. 28, 1997, now abandoned, which is a continuation of U.S. patent application Ser. No. 08/714,911, filed on Sep. 17, 1996, now abandoned, which is a continuation of U.S. patent application Ser. No. 08/540,728, filed on Oct. 11, 1995, now abandoned, which is a continuation of U.S. patent application Ser. No. 08/318,585, filed on Oct. 5, 1994, now abandoned, which is a continuation of U.S. patent application Ser. No. 07/861,065, filed on Mar. 31, 1992, now U.S. Pat. No. 5,364,002, which is a continuation-in-part of U.S. patent application Ser. No. 07/782,290, filed on Oct. 18, 1991, now U.S. Pat. No. 5,289,963, and the disclosures of each of the above-identified applications are hereby incorporated by reference in their entirety.

BACKGROUND OF THE INVENTION

1. Field of the Invention

The present invention relates to an apparatus and method for applying surgical staples to attach objects to body tissue. More particularly, this invention relates to a staple applier particularly adapted for attaching surgical mesh to body tissue to reinforce a surgical repair of the body tissue, as in hernia repair.

2. Background of the Invention

Hernias may be divided into three general classes: direct hernia, indirect hernia and femoral hernia. In a direct or indirect inguinal hernia, often a part of the intestine protrudes through a defect in the supporting abdominal wall to form a hernial sac requiring surgery which generally includes a surgical incision in the groin ranging up to six inches in length. Several layers of the abdominal wall are generally separated to reach the herniated portions. During the procedure, the hernia is closed outside the abdominal wall in a manner which resembles the tying of a sack at the neck. Often a surgical mesh is attached by sutures directly over the hernia repaired opening to provide a reinforcement to the opening.

Traditionally, such hernia repairs involved major invasive surgical procedures which often caused excessive trauma to the patient and necessitated unusually long post-operative recuperative periods. In addition, numerous complications, related directly or indirectly to the surgery often resulted, including bleeding, infection, testicular atrophy, organ damage, nerve damage, blood vessel damage, etc. Further, cutting through the numerous layers of tissue to obtain access to the herniated area often caused severe trauma to the patient. A detailed discussion of traditional hernia repair may be found in "Hernia Repair Without Disability, Second Edition", by Irving L. Lichtenstein.

Such invasive surgical procedures have also been utilized in other areas of the body, including surgery on the gall bladder, appendix, lungs and the like. For the reasons previously stated, the use of laparoscopic and endoscopic surgical procedures have been relatively popular and such popularity has provided additional incentive to develop the procedures further.

In laparoscopic procedures, surgery is performed in the interior of the abdomen through a small incision; in endoscopic procedures, surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues and vessels far removed from the incision, thereby requiring that any instruments be used in such procedures be long and narrow while being functionally controllable from one end of the instrument, i.e. the proximal end.

In hernia surgery, as compared to gall bladder surgery, certain procedures and instruments are the same, yet certain of the instrument requirements differ. For example, in hernia surgery a suitable mesh material is generally sutured over the opening in the tissue. The mesh material is often also attached by sutures and left within the opening to act as a reinforcing agent for tissue regrowth in the area of the surgery. One example of a mesh material currently utilized in hernia surgery includes a polypropylene material marketed by the Ethicon division of Johnson & Johnson, New Brunswick, N.J., under the trademark MARLEX. Another example of a mesh material is a tri-fluoroethylene material marketed by W.L. Gore & Associates, Newark, Del., under the trademark GORE-TEX.

As noted, during conventional invasive surgical procedures, such mesh materials are often sutured within the surgical opening or over the sutured opening by conventional suturing techniques. However, with the advent of laparoscopic surgery the need for suitable mesh attachment techniques through the relatively narrow endoscopic tubes or cannulas is clearly defined. Up to the present, such devices or staples suitable for mesh attachment have not yet been developed.

U.S. Pat. No. 4,944,443 to Oddsen et al. discloses an instrument and method for applying and forming staples into body tissue to suture a hernial opening. The staple is applied to two pieces of body tissue on opposite sides of the opening which are gripped, approximated and held together by a tissue positioning assembly. U.S. Pat. No. 4,919,152 to Ger relates to a surgical instrument for placing a single clip which is proposed for use in direct hernia repair for closing sacs having narrow neck openings.

Up to the present there remains a need for an apparatus which is particularly adapted to endoscopically apply staples for attaching objects such as surgical mesh to body tissue in a manner to positively secure the object to the body tissue without danger of separation thereof after the attachment is completed. The present invention relates to such an apparatus as well as a method for attaching such objects with staples particularly configured and adapted to accomplish these objectives.

SUMMARY OF THE INVENTION

An apparatus for endoscopic application of a surgical staple adapted to attach objects to body tissue, which comprises frame means, generally elongated endoscopic means connected to the frame means and extending distally therefrom, means for storing at least one surgical staple at the distal end portion, the staple configured and adapted to attach an object to body tissue, means for individually advancing the at least one staple distally for positioning adjacent the body tissue, and anvil means for closing the staple in a manner to encompass at least a portion of the object and to penetrate the body tissue to attach the portion of the object to the body tissue. Preferably, the apparatus for endoscopic application of surgical staples is adapted to attach surgical mesh to body tissue and comprises means for storing a plurality of surgical staples in generally stacked relation to permit configuring and dimensioning the endoscopic means for insertion into an endoscopic cannula tube. The staples are configured and adapted to attach the surgical mesh to body tissue, particularly for hernia related surgery. Further, the staple advancing system extends from the frame means to the endoscopic means and is activated by a trigger mechanism pivotally attached to the frame means and forming a part thereof.

The surgical staples are stored in stacked relation at the distal end of the endoscopic means. Also, the endoscopic means defines a longitudinal axis and the surgical staples are stacked to form an angle with the longitudinal axis, thereby improving visibility.

The surgical staple storing means is pivotally attached at the distal end portion of the endoscopic means wherein the surgical staple storing means is selectively pivotable by the user. Pivotal control means is located at the proximal end of the endoscopic section to pivot the surgical staple storing means from a proximal location. The location of the pivotal control means is provided for convenience and accessibility to the operator. The pivotal control means of the staple storing means comprises a member movable with respect to the endoscopic means in proximal and distal directions and adapted to position said surgical staple storing means at substantially zero degrees with respect to said longitudinal axis when said pivotal control means is in a first position and said surgical staple storing means forms an angle of up to about 45 degrees when said pivotal control means is in a second position.

The first position may be the proximalmost position of the pivotal control means and the second position may be the distalmost position corresponding to the staple storing means being pivoted up to about 45 degrees with respect to at least one side of the longitudinal axis. Further, the pivotal control means of the staple storing means may include a generally cylindrical movable member slidably positioned about a proximal portion of the endoscopic means.

The staple storing means may also comprise a rotatable sleeve positioned within the movable member and adapted to rotate in a first direction when the movable member is moved toward the proximalmost position and to rotate in the opposite direction when the movable member is moved toward the distalmost position.

The surface at the distalmost end portion of the rotatable sleeve may form an angle with respect to the longitudinal axis of the endoscopic means and the distalmost end surface of the rotatable sleeve may be positioned and arranged to engage elongated control means positioned within the endoscopic means for engagement with at least a portion of the staple storing means at a distal location of the endoscopic means whereby rotatable movement of said rotatable sleeve correspondingly produces longitudinal movement of said elongated control means. Preferably, the elongated control means comprises at least two elongated rods positioned within the endoscopic means and in engagement with the distalmost end portion of the rotatable sleeve at the proximal ends thereof and arranged to engage at least a portion of the staple storing means at respectively opposed locations such that rotation of the rotatable sleeve in a first direction produces distal movement of at least one of the rods and corresponding proximal movement of the other rod and rotation of the rotatable sleeve in the opposite direction respectively produces correspondingly respectively opposite movement of the rods.

The staple storing means includes an indentation adapted to receive each rod in engagement therewith and each rod is correspondingly configured at the distal end to engage the respective indentation to produce smooth rotation of the staple storing means when the rods are respectively moved distally and proximally. Further, the means for individually advancing the staples distally is user controllable at a proximal location. The means for individually advancing said staples distally comprises a plate member positioned adjacent and proximal of the lowermost staple and adapted to be movable distally whereby the plate member engages the lowermost staple and advances the staple in the distal direction. Also, the means to individually advance the staples comprises staple pusher means which comprises said plate member and the plate member is dimensioned, configured and arranged to engage and advance each staple distally.

The staple pusher means includes an elongated member of super elastic material such as NITINOL brand metal and is adapted to advance the staples and transmit closing force thereto. This member is further adapted to resiliently deform to facilitate pivoting movement to the staple storing means. The staple pusher means further comprises an elongated staple firing rod.

In the preferred apparatus the staple pusher means is biased to a pre-fired position by a constant force negator spring which prevents the operator tendency to rotate the hand, which occurs when a spring force increases.

Also a trigger mechanism is pivotally mounted for pivotal movement against the force of the negator spring when pivoted proximally to a position corresponding to advancing the pusher means distally to advance the staple next in line for closure.

The staple storing means includes anvil means positioned distally of the stack of staples and configured, dimensioned and adapted to be engaged by each said staple when said staple is advanced distally by said plate member.

The staples are each formed of a first length of wire having at least two leg portions at each end extending generally perpendicular to said first length of wire. The anvil means comprises at least two upstanding leg members positioned to be engaged by the first length of wire of each staple when the staple is advanced distally by the plate member. The leg members of the anvil means are dimensioned, positioned and arranged such that engagement by the first length of wire of each staple causes the leg members of the staple to fold inwardly toward the first wire due to the configuration of the staple and the corresponding configuration of the distalmost staple engaging edge of the plate member. The plate member is connected to elongated means comprised of super elastic member and the firing rod.

The means to move the elongated means and the plate member in distal and proximal directions is positioned within the frame means. Resilient means is positioned below each staple such that upon completion of closure thereof, and withdrawal of the staple advancing plate member the resilient means resiliently lifts the staple above the level of the anvil means. Also, the elongated means extends from the frame means through the endoscopic means whereby a distal portion thereof and the plate member are positioned within the staple storing means. The means to advance the elongated means and the plate member includes ratchet and associated pawl means adapted to prevent proximal movement thereof except when the staple advancing means is advanced to the distalmost position whereby the pawl means is released so as to permit return of the elongated member and the staple advancing plate member to the proximalmost position to advance the next staple of the stack of staples.

Preferably, the ratchet and pawl means comprises a ratchet member fixedly connected to the frame means and has a ribbed surface, and pawl means connected to the elongated plate advancing means and positioned adjacent the ratchet member and adapted to engage the ribbed surface. The ribbed surface is correspondingly configured and dimensioned to prevent proximal movement of the pawl means when the elongated plate advancing means is advanced at least partially in the distal direction. The ribbed surface of the ratchet member is comprised of a plurality of substantially and successive V-shaped peaks and valleys and the pawl means is configured at one end portion to engage the peaks and valleys in a manner which permits distal slidable movement thereof but prevents proximal movement thereof. Also, means is provided to release the pawl means when the pawl means is in the distalmost position corresponding to the distalmost position of the plate member and closure of the staple has been completed. A finger operative lever is adapted to produce distal movement of the elongated member and the plate member when said lever is pivotally moved.

The frame means has a pistol-like shape and includes a first member having a distal end connected to the endoscopic means and a manually gripping member at the proximal end is adapted to be gripped manually by the user. The endoscopic means is rotatable about the longitudinal axis and the pivotal control sleeve of the staple storing means is connected for rotation with the endoscopic means such that rotation thereof produces corresponding rotation of said endoscopic means. As described hereinabove, distal and proximal movement thereof produces pivotal movement of the staple storing means. The staple storing means is adapted to be pivoted up to about 45 degrees with respect to each side of the longitudinal axis whereby full pivotal articulation thereof is provided of about 90 degrees.

A surgical staple is adapted to attach objects such as mesh materials to body tissue which comprises, a length of wire having a central portion, a wire leg member extending generally perpendicular to the central wire portion at each end portion and adapted to penetrate the object and body tissue when positioned in adjacent engaged relation therewith and advanced thereinto. A bridge portion connects the central wire portion to each leg member and has a first generally arcuate portion generally concave and facing in a direction generally toward the center of the central wire portion. The inwardly facing concave portions are connected to each leg member by an arcuate portion having a generally concave configuration in the opposite direction so as to respectively engagably support each bridge portion against a pair of anvil members whereby applying force to the bridge portions causes the leg members to bend inwardly toward the central wire portion at respective locations inward of the first mentioned arcuate portions in a manner to form an acute angle relative thereto. The maximum distance between the central wire portion and each folded leg member is sufficient to grip the object and to penetrate the body tissue sufficient to attach the object to the body tissue. Each said leg member has a pointed tip to penetrate the object and the body tissue.

Each leg member of the staple has a tapered portion at the free end. The tapered portion on one leg member is located opposite the tapered portion on the other leg member whereby folding the leg members inwardly toward each other causes each tapered portion to respectively cam the other leg member whereby the leg members are folded toward each other in adjacent relation without interference with each other. The central wire portion is positioned inwardly of each bridge portion to facilitate gripping the object between the central wire portion and the leg members. Further, each leg member has a generally arcuate shape and has a concave portion thereof generally facing the other leg member. The surgical staple is preferably made of titanium. Also, the central wire portion includes a portion thereof which is positioned inwardly of the bridge portions in the body tissue gripping direction to thereby form a bight portion for gripping the object and body tissue in combination with the leg members.

A method is disclosed for endoscopically applying surgical staples to attach objects such as surgical mesh to body tissue comprising the steps of storing at least one surgical staple in endoscopic means having storing means positioned at the distal end portion and adapted for advancing and closing said staple, positioning the object adjacent the body tissue for attachment to the body tissue, and advancing the surgical staple distally so as to penetrate the object and the body tissue and to close the staple in a manner to attach the portion of the object to the body tissue. Preferably, a plurality of surgical staples are stored in stacked relation in the endoscopic means.

The invention relates to the combination of a cannula adapted for insertion into a body cavity, the cannula including valve means for sealing the cannula. An endoscopic surgical staple applier has a frame, and an endoscopic portion defining a longitudinal axis, and extending distally from the frame, the endoscopic portion configured and adapted for insertion into the cannula through the valve means in sealing engagement therewith. The endoscopic portion further includes a plurality of surgical staples in stacked relation, and means for individually pushing the staples through the distal end thereof is provided whereby staple closing means causes the staples to be closed while attaching an object such as surgical mesh to the body tissue. Seal means is positioned and adapted to obstruct passage of gaseous media from the body cavity.

A kit is also disclosed for endoscopic application of a surgical staple adapted to attach surgical mesh to body tissue in hernia repair, which comprises, surgical mesh, cannula means, and apparatus for endoscopic application of a surgical staple adapted to attach the surgical mesh to body tissue. The apparatus and staples of the kit are constructed according to the invention. The components may be supplied as part of a kit or they may be packaged in a blister-type or other package.

In an alternative embodiment, an apparatus is disclosed for endoscopic application of a surgical staple adapted to attach an object to body tissue, which comprises frame means, generally elongated endoscopic means connected to the frame means and extending distally therefrom, cartridge means for storing at least one surgical staple at the distal end portion, the staple being configured and adapted to attach an object to body tissue. Means is provided for individually advancing the at least one staple distally for positioning adjacent the body tissue, and anvil means is provided for closing the staple in a manner to encompass at least a portion of the object and to penetrate the body tissue to attach the portion of the object to the body tissue.

In the preferred embodiment, the apparatus includes on the elongated endoscopic means, means for engagably receiving and supporting the cartridge in a manner to advance the staples individually for endoscopic application.

A cartridge is also disclosed for containing a plurality of surgical staples for fastening body tissue which comprises housing means adapted to support the plurality of surgical staples, and means dimensioned, positioned and adapted to engage each staple as the staple is advanced from the housing means in a manner to prevent the staple from deforming out of the plane of the staple when the staple is deformed to attach the staple to body tissue.

The invention also relates to a system for attaching surgical mesh to body tissue adjacent a tissue repair within a body cavity which comprises, a frame, and an elongated endoscopic section connected at the proximal end thereof to the frame and extending distally therefrom, the endoscopic section configured and adapted for insertion into an endoscopic cannula within the body cavity. The endoscopic section includes a disposable cartridge adapted to store a plurality of surgical staples in stacked relation, the cartridge being removably engagably supported by a pivotal support member, each staple being formed of a first length of wire having at least one leg portion at each end extending generally perpendicular to said first length of wire, the leg portions being continuous with said first length of wire and configured to facilitate insertion into surgical mesh and adjacent body tissue therebeneath when said staple is advanced toward said mesh, the staple further being configured to facilitate folding said legs inwardly toward said first length of wire when at least a portion of the first length of wire is supported against anvil means, whereby said leg portions and said first length of wire grip said mesh and the body tissue therebetween to attach at least the gripped portion of the mesh to the body tissue. Means is provided for individually advancing the staples distally for positioning adjacent the mesh and the body tissue. Means is also included for providing perceptible tactile indicator when each staple is advanced to a predetermined position. Means is provided for closing each said staple while said staple is advanced toward said mesh and the body tissue so as to penetrate said mesh and the body tissue while causing said leg members to fold inwardly toward said first wire of said staple to grip said mesh and the body tissue between said first wire and said legs.

A method is disclosed for endoscopically applying surgical staples to attach objects such as surgical mesh to body tissue comprising the steps of storing at least one surgical staple cartridge positioned at the distal end portion and adapted for advancing and closing the staple, positioning the object adjacent the body tissue for attachment to the body tissue, and advancing the surgical staple distally so as to penetrate the object and the body tissue and to close the staple at least sufficient to attach said portion of the object to the body tissue.

A kit is disclosed for endoscopic application of a surgical staple adapted to attach surgical mesh to body tissue in hernia repair, which comprises surgical mesh, cannula means, and apparatus for endoscopic application of a surgical staple adapted to attach the surgical mesh to body tissue. The apparatus includes frame means, and generally elongated endoscopic means connected to said frame means and extending distally therefrom and dimensioned and configured for insertion into the cannula means. The endoscopic means includes a removable and replaceable cartridge for storing a plurality of surgical staples at the distal end portion, the staple configured and adapted to attach objects to body tissue, means for individually advancing the at least one staple distally for positioning adjacent the surgical mesh and the body tissue, and anvil means for closing the staple at least sufficient to encompass at least a portion of said surgical mesh and to penetrate said surgical mesh and the body tissue in a manner to attach the portion of the surgical mesh to the body tissue.

BRIEF DESCRIPTION OF THE DRAWINGS

Preferred embodiments of the invention are described hereinbelow with reference to the drawings wherein:

FIG. 1A is a perspective view of the distal end portion of the apparatus of FIG. 1 illustrating an alternative embodiment for pivoting the staple storage magazine;

FIG. 4 is a cross-sectional view taken along lines 4-4 of FIG. 3 illustrating the mechanism at the proximal end of the instrument for providing controlled distal movement to advance and to close staples at the distal end;

FIG. 5 is an enlarged cross-sectional view of the pawl and ratchet system in the handle which prevents proximal movement of the staple advancing system after distal movement has begun;

FIG. 6 is a view similar to FIG. 5 illustrating the pawl and ratchet system of FIG. 5 after a staple has been fired and during the proximal movement of the firing mechanism;

FIG. 8 is an enlarged cross-sectional view taken along lines 8-8 of FIG. 1 illustrating the rotating mechanism for the endoscopic portion and the system for pivoting the staple storage magazine from the proximal end;

FIG. 9 is a cross-sectional view taken along lines 9-9 of FIG. 8;

FIG. 10 is a cross-sectional view taken along lines 10-10 of FIG. 8 illustrating the system for providing pivotal motion of the staple storage magazine located at the distal end;

FIG. 15 is an exploded perspective view with parts separated, of the staple storage magazine which is controllably pivotally mounted at the distal end portion of the endoscopic section;

FIG. 16 is a cross-sectional view taken along lines 16-16 of FIG. 1 illustrating the distal end of the instrument including the pivotal staple magazine at three positions;

FIG. 17 is a cross-sectional view taken along lines 17-17 of FIG. 16 illustrating the staple next in line and the pusher plate provided for advancing the staple toward a staple closing anvil;

FIG. 18 is a cross-sectional view of the distal end of the instrument shown in engagement with a surgical mesh positioned against body tissue prior to firing the staple;

FIG. 19 is a cross-sectional view taken along lines 19-19 of FIG. 18;

FIG. 20 is a cross-sectional view similar to FIG. 18 during the firing of the staple and after penetration into the mesh and body tissue, but prior to closure;

FIG. 21 is a view similar to FIG. 19, taken along lines 21-21 of FIG. 20;

FIG. 22 is a cross-sectional view of the distal end of the instrument of the invention after closure of the staple in position to attach the surgical mesh to the body tissue;

FIG. 23 is a cross-sectional view taken along lines 23-23 of FIG. 22 illustrating the staple ejection system for releasing the closed staple from the anvils after firing;

FIG. 24 is a cross-sectional view similar to FIG. 22 illustrating the staple after closure about the surgical mesh and body tissue and the distal end of the instrument withdrawn from the surgical mesh;

FIG. 25 is a cross-sectional view taken along lines 25-25 of FIG. 24;

FIG. 26 is a cross-sectional view of the distal end portion of the staple storing magazine of the instrument after firing a staple;

FIG. 27 is a frontal view of a repair in body tissue illustrating one example of an arrangement of staples of the invention for attachment of reinforcing surgical mesh to the tissue;

FIG. 28 is a perspective view of a staple constructed according to the invention for attaching surgical reinforcing mesh to body tissue over a surgical repair;

FIG. 29 is another example of arranging the staples for attachment of the reinforcing surgical mesh to the body tissue in the area of a hernia repair;

FIG. 30 is a perspective view from above similar to FIG. 1, of an alternative embodiment of the present invention which includes a replaceable staple storing cartridge at the distal portion of the endoscopic section;

FIG. 31 is an exploded perspective view with parts separated, of the handle of the instrument of FIG. 30 illustrating a feature which provides perceptible tactile sensing of the pre-positioning of each staple prior to closing the staple with respect to the body tissue;

FIG. 32 is an exploded perspective view with parts separated, of the system at the distal end portion of the endoscopic section for pivotally supporting a replaceable staple storage cartridge;

FIG. 32A is an exploded perspective view of the staple storage cartridge with parts separated;

FIG. 32B is a view taken along lines 32B-32B of FIG. 32A, illustrating the "L" shaped staple holders on the bottom of the cartridge housing;

FIG. 34 is a plan view from above of the staple storage cartridge and related pivotal support member illustrating the feature of the invention which prevents each staple from rolling backwardly as they are deformed;

FIG. 35 is a cross-sectional view of the staple storage cartridge and related pivotal support member taken along lines 35-35 of FIG. 30;

FIG. 39 is a partial internal view of the handle portion and the staple storage cartridge illustrating the perceptible tactile staple pre-positioning feature of the invention;

FIG. 40 is a perspective view of the internal sleeve and pin which forms part of the pivoting system for the staple storage cartridge, similar to the sleeve disclosed in FIG. 13 in connection with the previous embodiment of the invention; and FIG. 41 is a cross-sectional view taken along lines 41-41 of FIG. 30, illustrating schematically gaseous seal means for the endoscopic section.

DETAILED DESCRIPTION OF THE PREFERRED EMBODIMENTS GENERAL

In general, the objective of the apparatus is to store a plurality of staples in the magazine as will be described in greater detail, and to individually advance each staple distally for closure about anvils while attaching a surgical mesh to the body tissue.

Following a general description of the present instrument, the description will be divided into separate sections to describe the structure and the desired movements produced thereby. Those sections include the handle section, the staple storage magazine pivoting system, the endoscopic section and staple firing system, the staple storage magazine, the staple closing system and the inventive staple. Also a kit for attaching objects such as surgical mesh is described.

The Instrument

Figure 1:
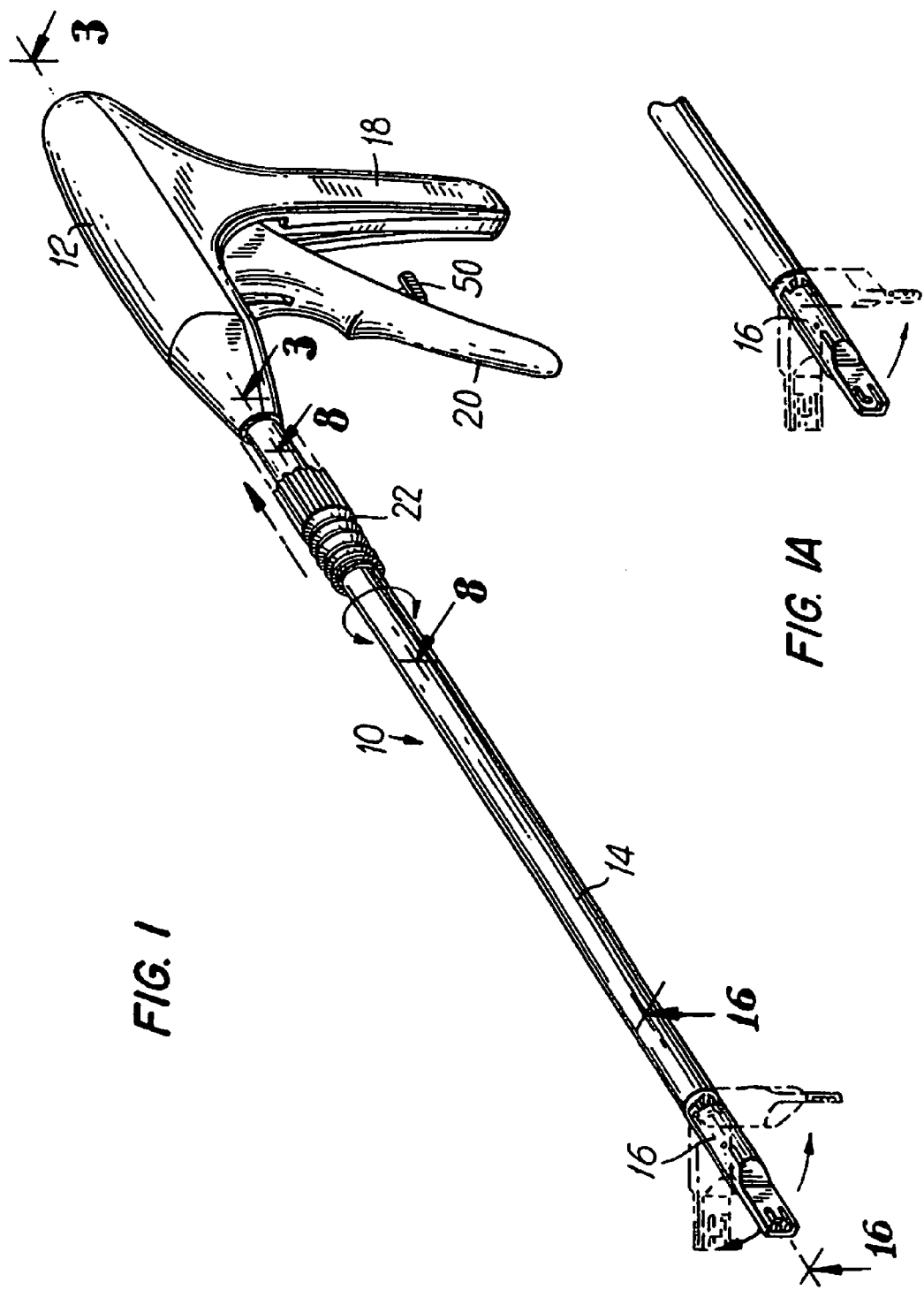
FIG. 1 is a perspective view from above, of an apparatus constructed according to the present invention for applying surgical staples to attach objects to body tissue.

Referring initially to FIG. 1 there is illustrated in perspective view the apparatus 10 particularly adapted for endoscopic application of surgical staples to attach surgical mesh to body tissue during hernia repair. Except where noted otherwise, the materials utilized in the components of the apparatus generally include such materials as polycarbonate for housing sections and related components, and stainless steel for such components which transmit forces. One preferred polycarbonate material is LEXAN brand polycarbonate available from General Electric Company. Other specific preferred materials such as nylon or glass filled nylon (for strength) are also utilized. However, equivalent alternative materials will readily come to the mind of those skilled in the art.

The apparatus 10 includes handle portion 12, and endoscopic section 14 having at the distal end portion a staple storage magazine 16 which pivots with respect to at least one side of the longitudinal axis extending centrally through the endoscopic section as shown in FIG. 1. Generally, staple storage magazine 16 will selectively pivot up to about 45 degrees with respect to the aforesaid longitudinal axis. In the illustration of FIG. 1 the staple storage magazine 16 is shown in general alignment with the longitudinal axis of the endoscopic section and in phantom to illustrate a range of movement. The total range of pivotal motion of the staple storage magazine 16 as shown is approximately 90 degrees, i.e. 45 degrees to each side of neutral.

Referring generally to FIG. 1, the handle 12 of instrument 10 includes manual grip 18 and pivotal trigger 20 which is pivoted toward and away from manual grip 18. Trigger 20 is pivoted toward manual grip 18 during the staple advancing and firing sequence which will be described in further detail. Trigger 20 pivots away from manual grip 18 to return the instrument to the pre-fired condition in position for firing the staple next in line.

A double knurled finger operative collar 22 is rotatable and adapted to rotate the entire endoscopic section 14 a full 360 degrees as will be described hereinbelow, while proximal movement of the finger ring 22 produces pivotal motion of the staple storage magazine to one of the positions shown in phantom in FIG. 1. To achieve the other position shown in phantom in that Fig., the collar 22 may be simply rotated 180 degrees thereby rotating the entire endoscopic section and causing the position of the magazine 16 to be reversed as shown to the other position shown in phantom. Thus, it can be seen that the combination of full rotation of the endoscopic section and the pivotal movement of the staple storing magazine facilitates a wide range of articulation of the distal end of the staple magazine 16, thus facilitating application of staples over a wide range of locations (±180 degrees) and in any of a plurality of orientations. In the embodiment of the invention shown in the Figs., when the collar 22 is moved to its proximalmost position the staple magazine is in one of the positions shown in phantom in FIG. 1, i.e. at an angle with respect to the longitudinal axis of the instrument. When the collar 22 is advanced to the distalmost position the staple magazine assumes the position shown in FIG. 1, i.e. in alignment with the longitudinal axis of the instrument.

Thus, in the preferred embodiment of FIG. 1, it can be seen that the full 90 degrees of movement of the magazine may be achieved simply by longitudinal movement of collar 22 in combination with full rotation of the endoscopic section. The longitudinal movement of collar 22 causes pivotal movement of the staple storing magazine to 45 degrees in one direction and rotation of the endoscopic section provides completion of the articulation of the magazine. Both of these movements in combination, facilitate a wide range of maneuverability of the distal end of the staple magazine 16, thus facilitating application of staples over a wide range of locations (±180 degrees) and in any of a plurality of orientations.

Alternatively, the positions of the staple storing magazine 16 may be achieved as shown in FIG. 1A, i.e. by movement of the magazine between zero degrees and about 45 degrees on either side of the longitudinal axis. In such arrangement, to achieve the positions shown in phantom in FIG. 1A, the collar 22 is moved distally and proximally, equal distances on either side of a neutral detent. Movement in one direction would pivot the magazine to one side and movement in the other direction would cause pivotal movement of the magazine in the opposite direction. The directions selected would be arbitrary. However, in this last described embodiment the orientation of the magazine would be the same throughout the 90 degree pivoting range, whereas in the preferred embodiment of FIG. 1, the orientation of the magazine when on one side is opposite the orientation when on the other. Further, in this embodiment the endoscopic section will be somewhat longer to accommodate the additional movement of collar 22.

The Handle Section

Figure 2:
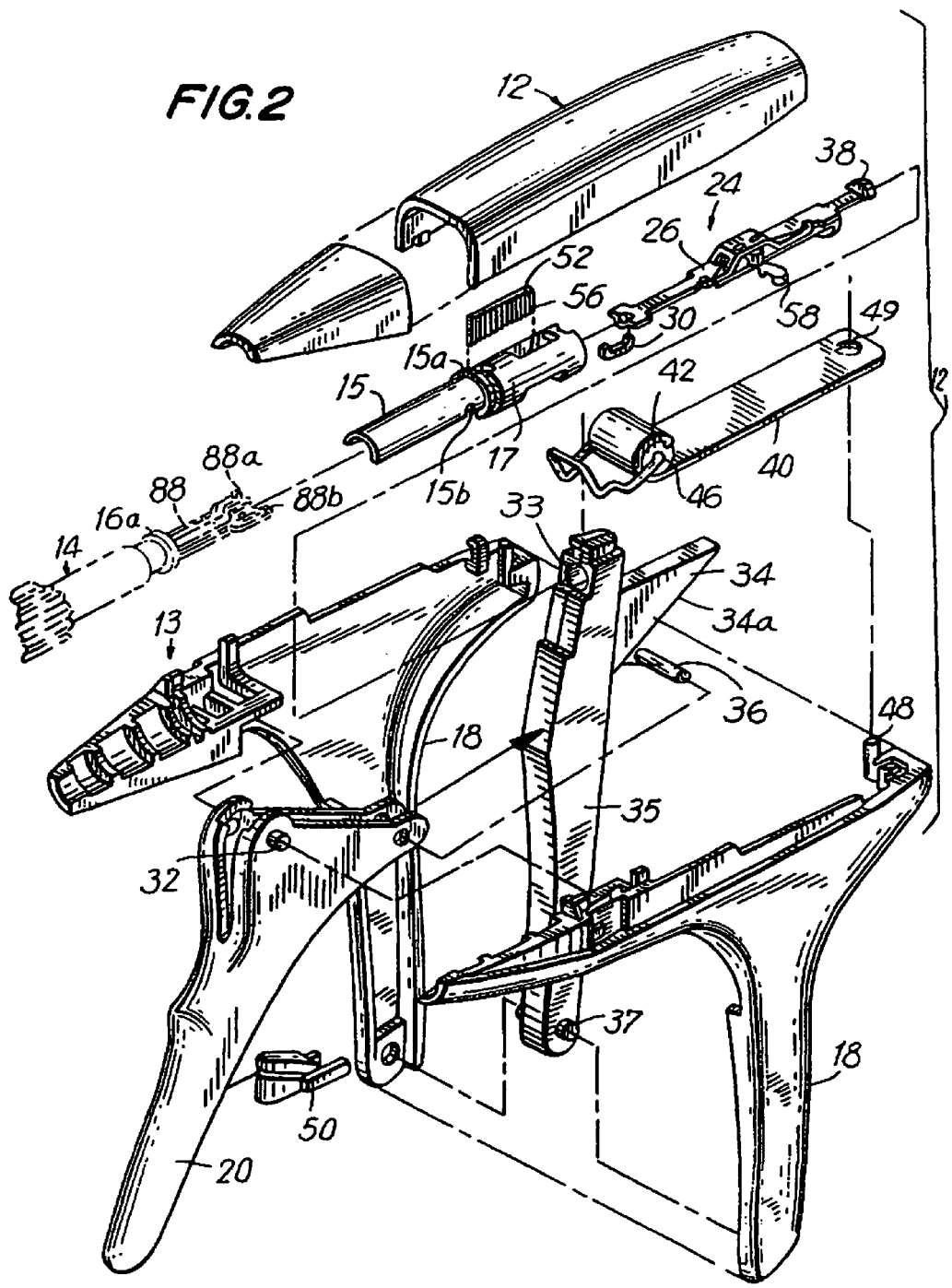
FIG. 2 is an exploded perspective view with parts separated, of the handle of the instrument of the invention and the associated components.
Figure 3:
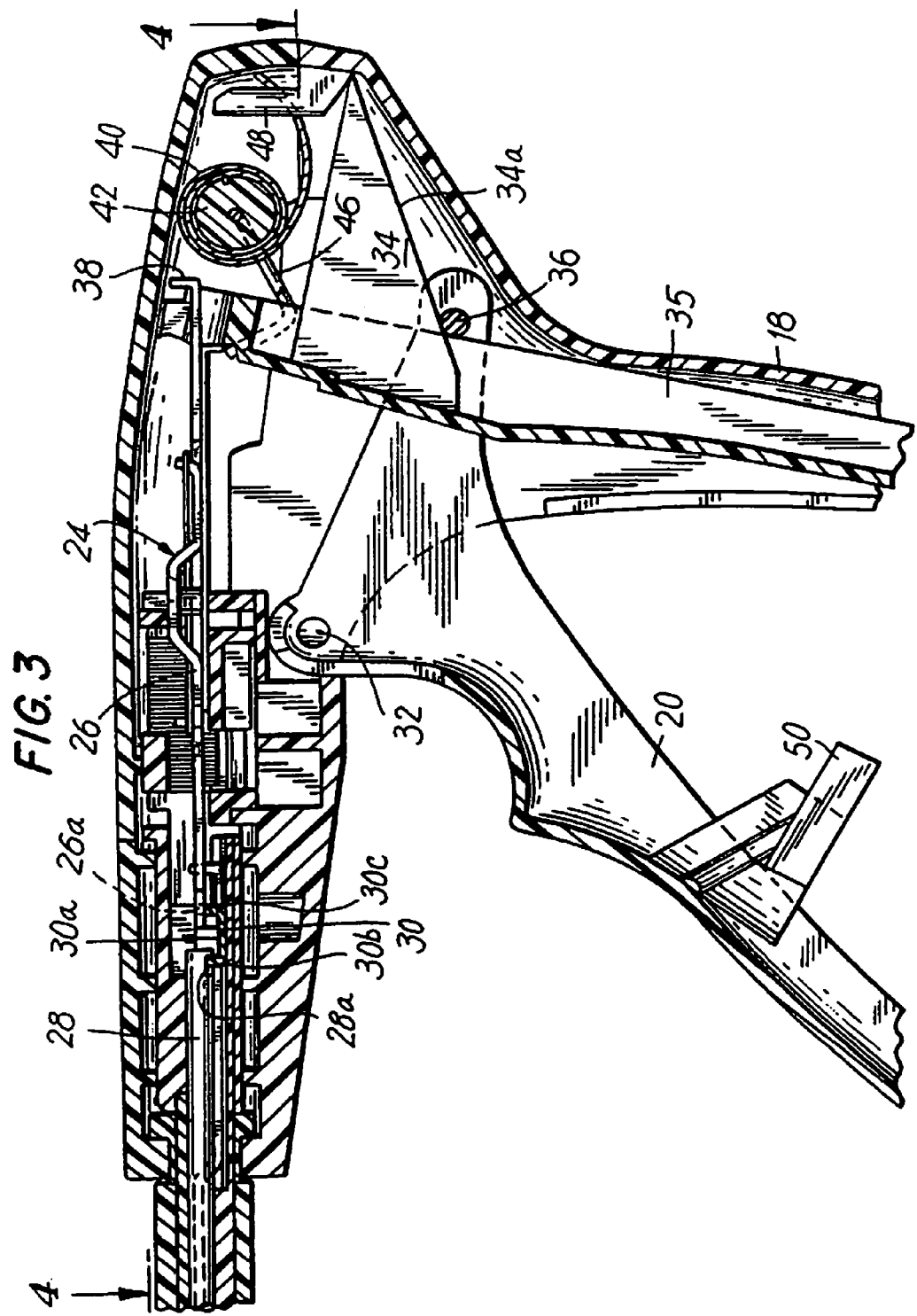
FIG. 3 is a cross-sectional view taken along lines 3-3 of FIG. 1, illustrating the handle mechanism of the instrument in the pre-fired condition.

Referring to FIG. 2, there is shown an exploded perspective view with parts separated, of the handle of the instrument with associated components. The handle is comprised of an outer housing preferably formed of separate sections as shown, of polycarbonate material. The separate parts shown are attached by welding, adhesives, etc. FIG. 3 illustrates a cross-sectional view of the handle mechanism taken along lines 3-3 of FIG. 1. The ultimate purpose of the handle mechanism is to provide controlled distal movement to the pusher assembly 24, a portion of which is shown in FIG. 2. The pusher assembly extends through the endoscopic section 14, a portion of which is shown in phantom in FIG. 2. In the embodiment shown, the endoscopic section shown is intended to be permanently and rotatably attached to the instrument via rim 16a formed on bushing 16 and rim 15a on half round sleeve 15. The instrument shown is contemplated to be entirely disposable. Half round sleeve 15 is integrally formed with barrel 17 which is in turn affixed to handle 12 at the nose piece 13.

However, it is also contemplated and within the scope of the invention to construct the endoscopic section to be selectively detachable whereby the handle may be sterilized and reused, or the endoscopic section can be sterilized, and the staple storage magazine re-loaded with staples for re-use. Alternatively a replacement staple magazine, and optionally a replacement endoscopic section, may be detachably secured to a disposable handle for multiple use during a single surgical procedure. Thus, any combination of alternatives may be incorporated within the scope of the invention.

Figure 7:
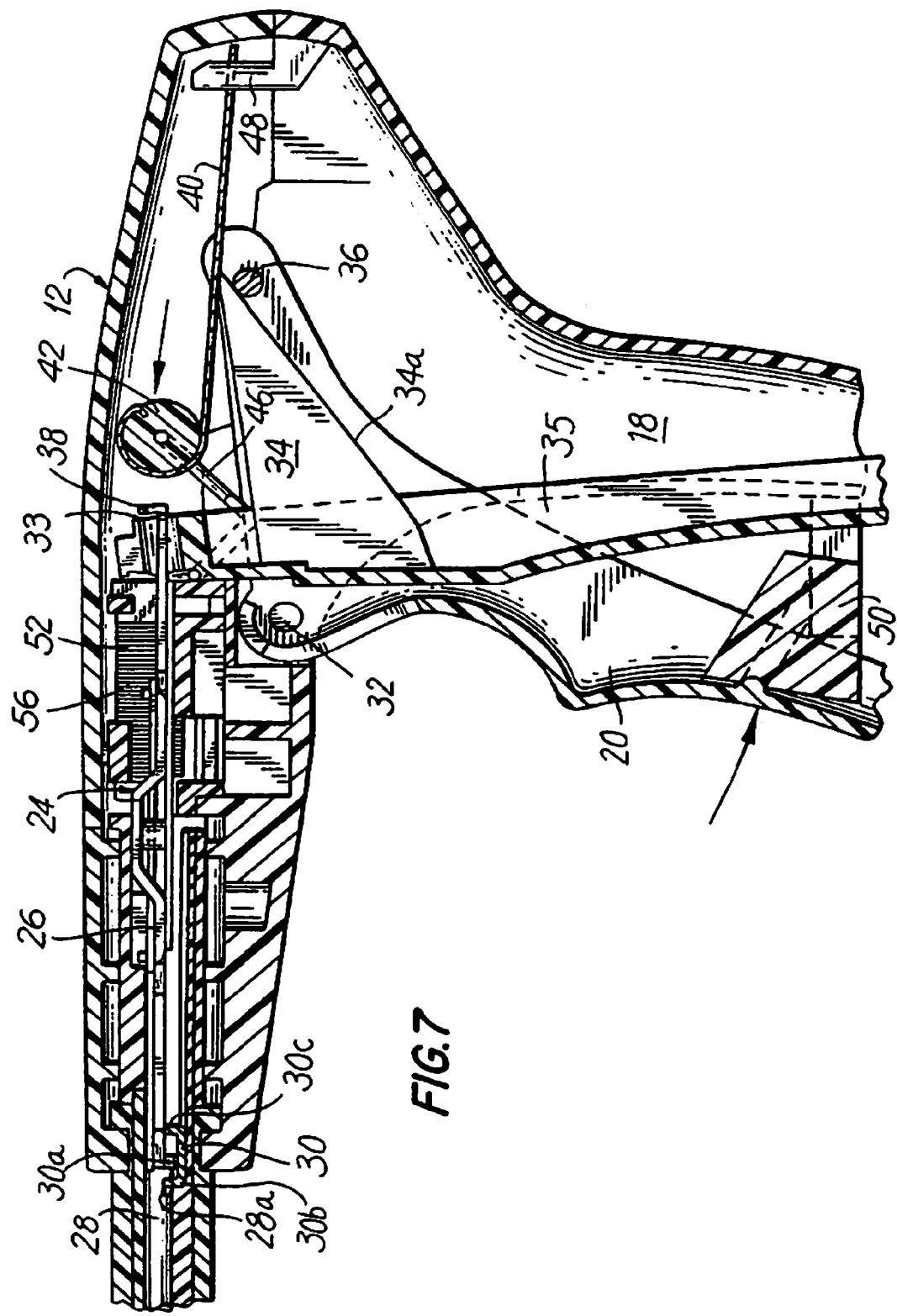
FIG. 7 is a cross-sectional view similar to FIG. 3 with the staple advancing actuating handle in the full proximal pivoted position corresponding to firing of a staple.
Figure 12:
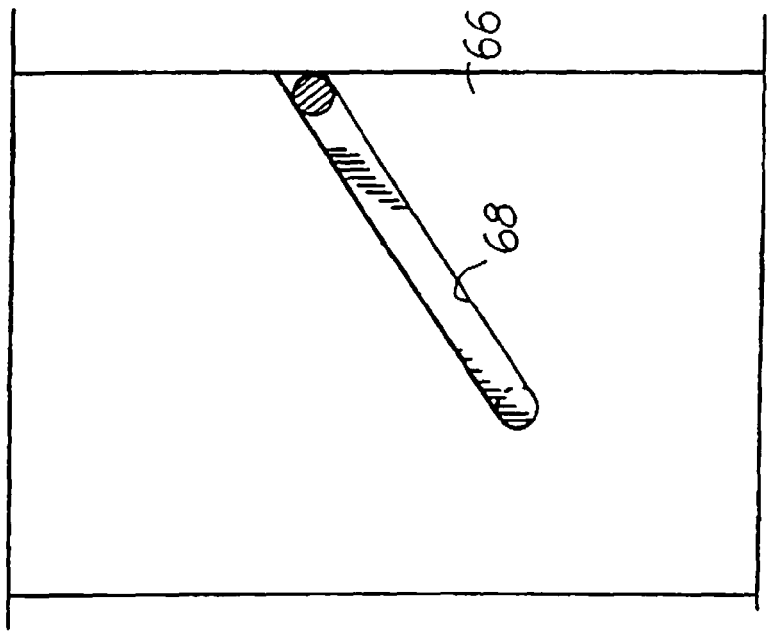
FIG. 12 is a view of the interior surface of the inner sleeve of the manually operable collar of FIGS. 8-11, projected as a flat surface to illustrate the helical groove provided for coaction with a pin to provide pivotal motion for the staple magazine at the distal end.
Figure 14:
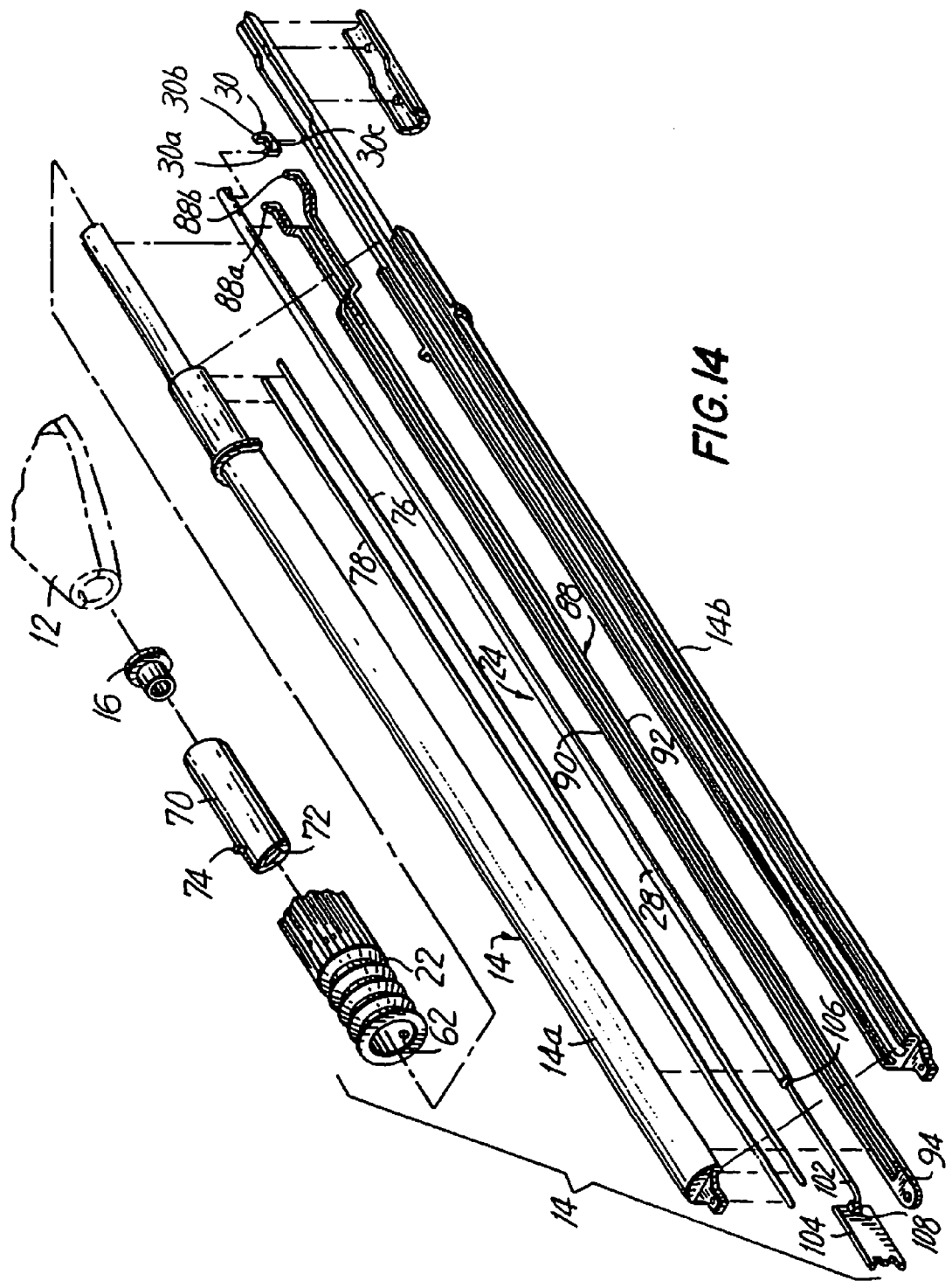
FIG. 14 is an exploded perspective view with parts separated, of the endoscopic section of the instrument of the invention, illustrating the staple advancing system and components thereof.

Referring now to FIG. 2 in conjunction with FIGS. 3, 7 and 14, pusher assembly 24 includes flanged thrust bar 26 connected to firing rod 28 by lost motion connector 30 as shown in FIG. 3. Lost motion connector 30 is a bar having a generally "U-shaped" configuration as shown. The lost motion connector 30 provides a positive connection between flanged thrust bar 26 and firing rod 28, yet provides a small space between the firing rod and the thrust bar 26 as will be described. Since the respective slots 28a and 26a in the firing rod 28 and in the thrust bar 26 are dimensioned slightly larger in width than the thickness of the legs 30b and 30c of the lost motion connector 30 which are received in these slots, a small degree of relative movement (i.e., about one tenth (1/10) of an inch) is provided permitted between the components in the staple firing chain. This small degree of movement is provided for several reasons as follows: 1) minor pivotal proximal movements of the trigger mechanism will not immediately result in engagement between the pusher assembly and the staple next in line, thus avoiding inadvertent distal movement of the staple during handling by operating room personnel, or positioning by the user; 2) engagement of the pusher assembly with the next staple will not occur until the pawl and ratchet plate of the clutch mechanism (described hereinbelow) takes place, thus preventing inadvertent partial advancement of several staples at a time. This would occur if the operator were allowed to partially activate the trigger mechanism several times over the same part of its cycle. The clutch mechanism prevents such movements. Further, this free movement of the thrust bar 26 also permits the staple advancing and forming components to engage each other smoothly without jamming or intercomponent interference with themselves and with the components of the system for pivoting the staple storage magazine 16 as will be described hereinbelow. Explanation of the pivoting system for the staple storage magazine will illustrate the advantages of the lost motion connector bar in further detail.

Trigger mechanism 20 is pivotally attached at pivot pin 32 for pivotal movement toward and away from handle grip 18, and is adapted to produce upward and downward rotational movement of triangular member 34 when horizontal pin 36, attached to trigger mechanism 20, traverses an upward arc whose center of rotation is located at pivot pin 32. Thus, it can be seen that when handle grip 18 is positioned in the palm of the user's hand and trigger mechanism 20 is squeezed toward handle grip 18, horizontal pin 36 traverses an upward arc while engaging the longer side 34a of triangular member 34 as shown. This movement causes triangular member 34 to rotate upward in a counterclockwise direction while upright member 35 to which it is attached, pivots forwardly about a point of rotation defined by pivot pin 37 located at the lowermost end of a handle grip 18 shown in FIG. 2.

As can be seen in FIGS. 2 and 3, pusher assembly 24 is connected to upright member 35 through aperture 33 such that inward squeezing of trigger mechanism 20 will cause the entire pusher assembly to advance distally against the constant force provided by negator spring 40 as shown. The negator spring 40 is formed of a resilient flat spring material coiled about the rotational bar 42 which is rotationally mounted about cross member 44 which forms part of bracket 46. The free end of negator spring 40 is attached to an anchor pin 48 via aperture 49 as shown, while the spring 40 is normally biased toward the coiled configuration as shown in FIG. 3. It can therefore be appreciated that after squeezing trigger mechanism 20 the full stroke from the position shown in FIG. 3 toward handle grip 18 to the position shown in FIG. 7, release of the trigger mechanism will permit the negator spring 40 to assume control and to return rotational bar 42 to the pre-fired proximal location by the automatic winding action of the negator spring 40 to its original unloaded configuration. This motion in turn causes the entire pusher assembly 24 to return to the proximalmost pre-fired position as shown in FIG. 3. The constant force of negator spring 40 uniquely prevents the natural tendency of the user to rotate the hand as with springs which increase in force when progressing through a full spring cycle.

Referring once again to FIGS. 2 and 3, trigger stop device 50 is attached to trigger mechanism 20 and is configured and dimensioned for engagement with handle grip 18 in a manner to thereby limit the proximal pivotal movement of trigger mechanism 20. Depending upon the particular limits required in the apparatus, trigger stop device 50 can be dimensioned accordingly.

Referring now to FIGS. 4-6, the structure and function of the uni-motion clutch mechanism will be described. This clutch mechanism prevents proximal movement of the pusher assembly in the event the trigger mechanism is released after the squeezing motion of the trigger mechanism and the advancement of the pusher assembly has begun but before the full stroke is completed. The clutch mechanism is self-releasing when the pusher assembly reaches the distalmost position, thus permitting the entire pusher assembly to return to the pre-fired, or proximalmost condition, and the trigger mechanism to also return to the pre-fired position.

Referring now to FIG. 4 in conjunction with FIGS. 5 and 6, ratchet plate 52 is fixed to barrel 17 and therefore fixed with respect to the handle housing and possesses a surface defined by a plurality of right angle triangular shaped parallel ridges 56 as shown in FIGS. 4-6. Pawl 58 is rockably mounted for distal and proximal movement with pusher assembly 24 through barrel 17, and is biased toward ratchet plate 52 by resilient wire spring 60 as shown. The location of pawl 58 shown in FIG. 4 corresponds to the pre-fired condition of the apparatus with negator spring 40 in the fully wound position and pawl 58 located proximal of ratchet plate 52. Further, pawl 58 is preferably of stainless steel while ratchet plate 52 is made of brass or other compatible material.

While trigger mechanism 20 is squeezed toward handle grip 18 producing distal motion of the entire pusher assembly 24, pawl 58 engagably slides distally past the ratchet surface 56 of ratchet plate 52 as shown in FIG. 5 such that one corner of the tip 62 of the pawl 58 sequentially engages each right angled ridge of ratchet plate 52 to thereby prevent proximal movement of the pusher assembly in the event the trigger mechanism is released by the operator. The engagement of pawl 58 with ratchet plate 52 provides audible confirmation that the pusher assembly is moving distally since the user will hear a series of progressive audible clicks. This action—which is best shown in FIG. 5—continues with the tip 62 of pawl 58 sliding past the ratchet surface of the ratchet plate 52 until the pawl is positioned distally of the distalmost tooth.

After completion of the staple firing stroke and upon release of the trigger mechanism 20 the pawl 58 moves proximally with the pusher assembly as described under the action of spring 40. The end portion 62 of pawl 58 which is now free, engages the distal end of the ratchet plate 52 causing the pawl to rock to the reverse direction shown in FIG. 6 so as to slide proximally past the ratchet surface of ratchet plate 52 without interference to the proximal movement of the pusher assembly 24. Thus, it can be seen that the clutch mechanism as described will effectively permit squeezing the trigger mechanism 20 toward the handle grip 18 while maintaining all positions midway through the stroke in the event the operator releases the grip, while permitting return motion thereof after the stroke has been completed. The clutch mechanism also allows the operator to advantageously preposition a staple such that the legs of the staple protrude from the distal end of the staple magazine discussed hereinafter, and then to release pressure from the trigger mechanism. The operator may then turn full attention to locating the prepositioned staple in the desired target location, at which point the pivoting of the trigger mechanism may be resumed and the cycle completed. This staple prepositioning greatly facilitates staple placement.

The Staple Storage Magazine Pivoting System

Referring to FIGS. 8-14, the system for pivoting the staple storage magazine located at the distal end of the endoscopic section 14 will now be described. FIG. 8 illustrates double knurled finger operable collar 60 which is mounted for rotation with the endoscopic section 14 by inwardly extending pin 62 which is slidably positioned within longitudinal groove 64 in the outer housing half section 14a of endoscopic section 14, as shown in further detail in FIG. 14. Thus collar 60 is readily slidable distally and proximally while pin 62 slides within groove 64. Thus while permitting slidable movement of collar 60, pin 62 prevents independent rotation of collar 60 relative to the endoscopic section 14. Accordingly, when collar 60 is gripped between the user's fingers and rotated, the endoscopic section 14 rotates with the collar.

Figure 11:
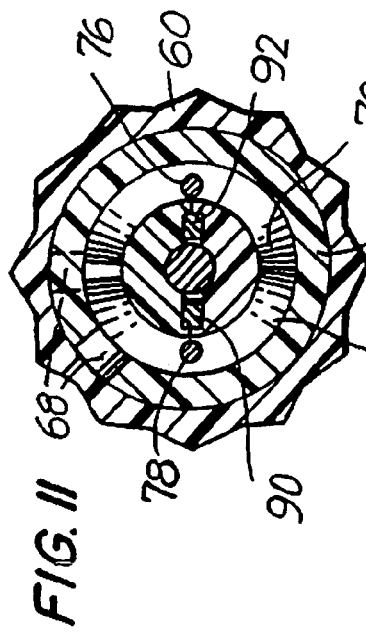
FIG. 11 is a cross-sectional view taken along lines 11-11 of FIG. 9 illustrating further details of the system for providing pivotal motion to the staple magazine at the distal end.

Positioned within finger operable collar 60 is helically grooved inner sleeve 66 fabricated of a suitable plastic material such as nylon, glass filled for strength. Helically grooved inner sleeve 66 is generally cylindrical in shape and includes a helical groove 68 shown in phantom lines in FIG. 8 and illustrated schematically in the projected frontal view of the sleeve shown in FIG. 12. The sleeve 66 is fixedly attached to outer collar 60 for rotation therewith. In the projected view of FIG. 12, the helical groove appears as a diagonal groove having a linear shape. In FIG. 11, finger operable collar 60 is shown in cross-section and the inner helically grooved sleeve 66 is shown whereby helical groove 68 is represented at two locations as viewed in FIG. 11. In FIG. 11, the cross-section of groove 68 at the 10 o'clock position (where lines 11-11 are located in FIG. 9) is just distal of the cross-section of groove 68 shown in phantom at the 12 o'clock position.

Referring now to FIG. 8 in conjunction with FIGS. 9-13, elongated internal cylindrical sleeve 70 is positioned partially within inner helically grooved sleeve 66 and collar 60 when collar 60 is in the distalmost position, as shown in FIG. 8; however, when collar 60 is withdrawn to the proximalmost position as shown in phantom lines in FIG. 8, the major portion of internal cylindrical sleeve 70 is positioned within collar 60 as shown. Internal sleeve 70 is preferably of nylon (preferably glass filled for strength) and defines a distal face 72 which is generally oriented at an acute angle with respect to the longitudinal axis of the instrument as shown clearly in FIGS. 8 and 13. The sleeve 70 contains pin 74 extending radially outwardly from the outer surface as shown. Pin 74 is preferably of steel or it may be formed of nylon integral with sleeve 70. Pin 74 is positioned for slidable movement within the helical groove 68 of inner sleeve 66 of collar 60 such that proximal movement of collar 60 will cause pin 74 to follow the groove 68 causing sleeve 70 to rotate in one direction. Similarly, distal movement of collar 60 to the position shown in phantom lines in FIG. 7 will cause pin 74 to traverse groove 68 in the opposite direction thereby causing sleeve 70 to rotate in the opposite direction.

The significance of the rotational motion of sleeve 70 as it pertains to the pivotal motion of staple storing magazine 16 will be described in further detail hereinbelow. At this stage, however, it is sufficient to state that the obliquely oriented distal face 72 of sleeve 70 engages the proximal ends of a pair of longitudinally extending push rods 76,78 shown in phantom lines in FIG. 13 and more clearly in FIG. 14 such that when collar 60 is moved distally or proximally, inner sleeve 70 also rotates and the rods 76,78 respectively move in equal and opposite directions by the engagement with different portions of oblique distal face 72 with these rods. In essence, one rod is engaged by a surface portion distal of the surface portion on the side of face 72 which engages the other rod. Thus, when the sleeve 70 is rotated in one direction, rod 78 moves in the distal direction while rod 76 withdraws proximally the same distance, and when sleeve 70 is rotated in the opposite direction, rod 76 moves in the distal direction and rod 78 moves proximally the same distance.

Collar 60 contains rotary ridges 60a in the distal half and longitudinal ridges 60b in the proximal half, and is thus conveniently movable longitudinally and rotatably by the user when the appropriate knurled portion is gripped between the user's fingers. However, the operator need not grip the collar 22 at any specific locations. The ridges may be formed integral by molding procedures or alternatively may be in the form of knurled surfaces. The rotary ridges respectively permit collar 60 to be finger movable distally and proximally, while the longitudinal ridges assist in rotation of collar 60 by hand. Rotational motion of the collar causes the endoscopic portion 14 to rotate while proximal movement of the collar in a preferred embodiment causes staple storing magazine 16 to pivot up to about 45 degrees in one direction with respect to the longitudinal axis of the instrument as shown in FIG. 1. Distal movement of the collar 60 to the distalmost position shown in FIG. 8, causes staple storing magazine 16 to withdraw to the original orientation shown in FIG. 1 which is generally in line with the endoscopic section. Thus, by pivoting the staple storing magazine up to 45 degrees and by rotating the endoscopic portion 14, the total range of movement of the staple storing magazine is 45 degrees to either side of the endoscopic section traversing a total of 90 degrees of effective pivotal movement. With respect to movements of collar 60, the direction which produces pivotal motion of staple storage magazine 16 away from the longitudinal axis or toward the axis is clearly a matter of choice and would be determined by the respective configurations of the coacting components.

In the alternative embodiment shown in FIG. 1A, the internal sleeve 70 and forward face 72 are configured such that collar 22 may be positioned midway between proximal and distal positions. The mid-position will correspond to the staple storage magazine being at zero degrees with respect to the longitudinal axis. Collar movement in one direction from neutral will produce up to 45 degrees of pivotal movement of magazine 16 and collar movement in the other direction on the side of neutral will produce pivotal movement of the magazine 16 up to 45 degrees in the other direction. A major distinction in this embodiment is that the actual orientation of the magazine with respect to the longitudinal axis will differ on either side of neutral.

Referring now to FIGS. 15 and 16, the system for providing pivotal motion to the staple storing magazine 16 is illustrated at the distal end of the instrument. In FIG. 16 the staple storage magazine 16 is shown in the position generally in alignment with the endoscopic section and is shown in phantom lines at the pivoted locations corresponding to plus or minus 45 degrees. The staple storage magazine is formed of an outer housing of a suitable plastic material such as polycarbonate and is comprised of upper housing half section 16a and lower housing half section 16b attached by welding, adhesives, etc. The upper housing half section 16a contains an indentation 80 at the proximal end having a "V-shaped" cross section and the lower housing half section 16b contains a similar indentation 82 also having a "V-shaped" cross section as shown. Both indentations 80,82 are adapted to respectively engagably receive the distal ends of rods 76,78 (which are rounded) such that when the rods are respectively and alternately moved in the proximal and distal directions as described hereinabove, one rod may advance distally to cause the upper housing to rotate and the other rod withdraws to permit the pivotal motion of the staple magazine. For example, as shown in FIG. 16, when rod 78 moves distally, engagement of the tip of the rod 78 with indentation 80 in upper housing 16a of staple storing magazine causes the staple magazine to pivot downwardly as shown in phantom.

Similarly, equal and oppositely withdrawing rod 76 will accommodate the downward movement of the staple storing magazine 16. In a similar fashion when the collar 60 is moved in the opposite distal direction the movement of each rod is respectively reversed causing rod 76 to move distally and to engage the lower housing 16b of staple storing magazine 16 and rod 78 withdraws to accommodate the pivotal movement of staple storing magazine back to the original (or neutral) position in general alignment with the endoscopic section as shown in FIG. 16. The lost motion connector 30 clearly provides a minor degree of space (i.e. about 1/10 inch) between the components, which space provides the advantages mentioned previously.

Alternatively one rod may be provided and connected to the staple storage magazine and adapted to pivot the magazine by causing such rod to move proximally and distally thereby actually pivoting the magazine about the pivot point.

The endoscopic section 14 is shown clearly in FIG. 14 and is mounted for rotation relative to the handle section 18. As noted above, the endoscopic section may be permanently attached to handle 12 as shown in a disposable instrument; alternatively as noted above, it may be removably attached to a re-usable handle, or a variety of other combinations or configurations.

The Endoscopic Section

Referring again to FIG. 14 the endoscopic section is shown in exploded view with parts separated for convenience of illustration and includes upper housing half section 14a and lower housing half section 14B. The housing half sections are preferably of a polycarbonate material such as LEXAN brand material mentioned previously, and are attached by welding, adhesives, etc. Positioned within the upper and lower housing half sections is pusher assembly 24 as described in more detail below, and anvil extension 88, formed of stainless steel and having a pair of elongated legs 90,92 which are joined at 94 at the distal end and which contain upwardly extending feet 88b,88b at the proximal end. As shown in FIG. 15, anvil extension 88 is attached at the distal end 94 to the staple storing magazine 16 by pivot pins 89 where the staple storing magazine is pivotally attached. The proximal connection points of anvil extension are best illustrated in FIG. 2 wherein upwardly bent feet 88a,88b are positioned within slots 15b in half round collar 15 which is fixedly attached to handle housing 12 by barrel 17 and nose piece 13 and related support members provided therein.

Anvil extension 88 is fabricated of stainless steel and its purpose is to stabilize the dimension of the endoscopic section 14 to prevent the forces acting on the components from stretching or compressing the upper and lower housing half sections 14a, 14b of the endoscopic section which are constructed of a polycarbonate material such as LEXAN brand material. Thus, the steel anvil extension provides dimensional stability to the endoscopic section while the endoscopic section is supporting the components being subjected to forces for supporting, advancing and forming the surgical staples as will be described.

The Staple Firing System

Referring further to FIG. 14, the steel pusher assembly 24 is formed of firing rod 28 connected to flexible elongated firing wire 102 which is in turn connected to pusher plate assembly 104 as shown. The connection between firing rod 28 and firing wire 102 is a crimped or swaged connection at 106, whereas the connection between firing wire 102 and pusher 105 is accomplished by an interference fit between the firing wire 102 and collar 108 which is attached to pusher plate 104. Firing rod 28 and pusher plate 104 are preferably made of stainless steel whereas firing wire 102 is made to be resiliently flexible to accommodate the pivotal movement of the staple storing magazine 16 since firing wire 102 is located within the instrument at the location of staple magazine 16. In particular, firing wire 102 is preferably made of a super elastic metal. One example of such super elastic metal is NITINOL brand metal available from Raychem Corporation, Menlo Park, Calif. This material has a reduced tendency to fatigue after a substantial number of cycles of deflection caused by pivoting the staple storage magazine. Other resilient materials are also contemplated for firing wire 102.

The Staple Storage Magazine

Referring now to FIGS. 15 through 18, there is illustrated further details of the staple storing magazine 16. As noted previously, the staple storing magazine 16 is comprised of upper housing half 16a and lower housing half 16b suitably attached by welding, adhesives, etc. The magazine is adapted to contain a plurality of surgical staples 110 which are particularly shaped to penetrate and to attach surgical mesh to body tissue. For particular details of the shape of the staples constructed according to the invention, reference is made to FIG. 28.

Referring once again to FIGS. 15-18, a particular feature of the present invention resides in the system of storage of the staples 110 which are positioned in adjacent stacked relation whereby the stack of staples forms an angle with the longitudinal axis of the instrument of approximately 45 degrees as shown in FIG. 18. one purpose of stacking the staples as shown is to provide greater visibility to the user by the fact that the outer surface of the upper housing half section adjacent the stack of staples forms a similar angle and provides visibility to the user at the distal end of the staple storage magazine. Angular stacking of the staples as shown greatly facilitates storage of a plurality of staples in a structure configured and dimensioned for use in endoscopic applications, e.g., for use through a trocar guide tube of diameter of about 12 mm for example. The stack of staples 110 as shown in FIG. 18 is positioned and retained in such position by a resilient spring member 113 having dual resilient legs and whose side profile is curved as shown in FIG. 18.

The distal end of each leg engages the uppermost staple follower 114 in the form of a nylon insert having a general "H-shaped" configuration and dimensioned sufficient to cover the staples as best shown in FIG. 15. The nylon follower is intended to transmit the downward force of the staple retainer spring 113 so as to distribute the force on the stack of staples in a manner to facilitate a constant and uni-directional downward force on the lowermost staple which is positioned for advancement and deformation. It also functions to advance the stack of staples downwardly when the lowermost staple is fired. Steel anvil plate 120 is shown in FIG. 15 and includes upwardly extending feet 116 and 118 which form anvils at the distal end as shown in FIG. 15, for forming the staple therearound.

Thus, as seen in FIG. 18, the lowermost staple is identified by numeral 110L and is in a position for engagement by pusher plate 104 when the pusher assembly is advanced distally. The pusher plate 104 is shown clearly in FIGS. 15 and 18 and contains distally advancing lands 104R and 104L shown clearly in FIGS. 15 and 19 at the distal end to facilitate transmission of advancing force to the two rounded or arcuate bridge portions of the staple. This relative complementary configuration of the pusher plate 104 and the staple 110 facilitates efficient and uniform distribution of force to the staple when it is deformed about the anvil members as will be described.

The Staple Closing System

Referring now to FIGS. 17-24 there is illustrated the sequential views of the staple advancing and closing system between the pre-fired and fired condition of the staple. In particular, the staple and pusher mechanism are shown in FIG. 17 in the pre-fired condition while the staple shown in FIG. 24 is embedded within the body tissue in a manner to retain the surgical mesh to the body tissue.

In FIG. 17, the staple pusher assembly 24 is positioned proximal of the lowermost staple 110L and pusher plate 104 is correspondingly positioned proximal of the lowermost staple 110L. In FIGS. 18 and 19 the pusher plate 104 has been partially advanced distally and the lowermost staple 110L has been advanced distally of the stack of staples 110 in a manner such that the pusher plate 104 has now replaced lowermost staple 110L thereby preserving the integrity and position of the stack of staples 110. The preservation of the stack of staples 110 is provided by the fact that the thickness of the staple pusher plate 104 is either identical to or slightly less than the thickness of the staples to assume that the plate 104 will engage only one staple at a time.

Referring further to FIGS. 20 and 21 the pusher plate 104 has now advanced distally sufficient to cause the staple to penetrate the surgical mesh 112 and the body tissue 114. As shown in FIGS. 20 and 21, it can be seen that anvil members 116 and 118 are positioned for engagement by the straight sections of bridge portions 110BR and 110BL of the back rib of the staple 110L such that engagement of the staple by pusher plate 104 with the arcuate end corner portions of the staple as shown will cause the staple to deform in a predetermined manner as will be described.

In FIGS. 22-24 the staple 110L is now shown in the deformed condition about the anvil members 116 and 118 and the straight portions 110S of the back rib of the staple 110 are still in engagement with the anvils 116,118. In FIG. 22, the staple has penetrated into the body tissue 114 and has been deformed and in FIG. 24 the staple deformation is completed in a manner to substantially retain the surgical mesh 112 in attached position with respect to the body tissue as shown in FIG. 22. The inwardly projecting central portion or bight, 110C, of staple 110 is shown gripping the mesh and tissue in cooperation with the staple legs as shown in FIG. 24. However, release of the staples from the anvil members 116,118 has not yet been completed.

Release of the staple from the anvil members 116,118 is readily accomplished by ejector spring 124 which is a "U-shaped" resilient spring having upwardly biased legs 124R and 124L each positioned respectively as shown in FIG. 15. When the pusher plate 104 is in the position shown in FIG. 20, the legs 124R and 124L of staple ejector spring are retained in a downward position by lands 104R and 104L of the pusher plate 104. However, when the pusher plate 104 is moved to the distalmost position shown in FIG. 23, the absence of the pusher plate permits staple ejector legs 124R and 124L to resiliently deflect upwardly to their natural configuration thereby creating a vertical separation between the anvil members 116,118 and the deformed staple, thus releasing the deformed staple from the anvil members as shown in FIG. 23. Continued proximal movement of the pusher plate 104 causes withdrawal of the pusher plate to a position entirely proximal of the stack of staples 110 as shown in FIG. 26, causing the stack of staples to move downwardly due to the downward force of resilient staple retainer spring 113 to advance the lowermost staple to the firing position.

Once the staple 110 is applied to the mesh 112 and tissue 114 as shown in FIGS. 22 and 24, the distal end of staple storing magazine 16 is withdrawn as shown in FIG. 24 and preparation is made for application of the next staple. FIG. 25 is a cross-sectional view taken along lines 25-25 of FIG. 24 with the staple storing magazine withdrawn from the surgical mesh and body tissue. Thereafter, the apparatus may be repositioned to apply another staple, or even an array of staples as shown in FIGS. 27 and 29.

Referring once again to FIG. 27, there is illustrated one form of surgical mesh repair of an opening in the body utilizing the apparatus and staple according to the invention. In the application shown in FIG. 27, a surgical mesh is attached to the body tissue over the opening as illustrated schematically at 114c in FIG. 27, and staples 110 have been applied in a circular array as shown to reinforce the repair. Beneath the mesh, the opening 114c may have previously been repaired as well. In FIG. 29 an alternative array of staples to apply mesh material to body tissue is shown. In this embodiment the mesh material 112 is essentially formed as a circular patch and staples 110 are oriented in a radial direction and are attached around the periphery of the patch such that one leg of the staple pierces the mesh and the other leg pierces body tissue 114. Essentially the staple bridges the periphery of the mesh material as shown. Clearly, alternative forms and arrangements are available to attach mesh or other surgery related objects or prostheses to body tissue as may come to the mind of persons skilled in the art.

It should be further noted that the repair of body tissue utilizing surgical mesh as shown in FIGS. 27 and 29 are exemplary, and that other applications of mesh and staples may be utilized in a manner to either reinforce a surgical repair or to encourage tissue growth. Such mesh materials are typically disclosed in U.S. Pat. Nos. 4,838,884, 4,665,221, 4,452,245, and 4,347,847. It is noted that the staple constructed according to the invention as shown in FIG. 28 is particularly adapted for attachment of such mesh material to body tissue according to any number of techniques which may readily come to the mind of those skilled in the art. In fact, in some instances the mesh may be formed as a plug for insertion into a surgical opening and then stapled. Moreover, the apparatus and staple of the present invention may be applied to attach other objects to body tissue as may come to the mind of those skilled in the art.

The Staple

Referring now once again to FIG. 28, there is illustrated the inventive staple 110 constructed according to the invention. The staple 110 is particularly shaped as shown, and is preferably formed of a length of wire of titanium. Stainless steel or equivalent material is also contemplated and the staple preferably has a rectangular cross-section as shown. Other cross-sections may be used. Typically, the wire will be about 0.38 mm in width (dimension w) and 0.51 mm in thickness (dimension T). The initial width of the staple before closure (dimension A) is about 4.4 mm and the thickness dimension between the back rib and legs after closure (i.e. dimension B in FIG. 24) is about 3 mm. Another example is a wire having a width of about 0.51 mm (dimension W) and a thickness of about 0.38 mm (Dimension T). The width before closure (dimension A) is about 8.64 mm and the thickness between the back rib and legs after closure is about 2.5 mm (dimension B in FIG. 24). The staple 110 has a central bight portion 110c and a wire leg member 110R and 110L extending generally perpendicular to the central portion as shown. Each leg member 110R, 110L is connected to the central portion 110c by a bridge portion 110BR, 110BL having an arcuate corner portion as shown. Each leg member has a sharp tip for penetrating mesh and body tissue. Right leg member 110R further possesses a tapered surface 110TR at the tip which is opposite the position of the tapered surface 110TL at the tip of the other leg member 110L as shown in FIG. 28.

When the staple shown in FIG. 28 is advanced toward dual spaced anvils 116,118 as shown in FIG. 21 for example, and staple pusher plate 104 as shown, engages the arcuate portions of the bridge portions 110BR and 110BL, the legs of the staples are made to fold inwardly toward each other as shown for example in FIG. 22, with one leg crossing over the other. The cross-over configuration is automatically assumed by the legs because of the presence of tapered surfaces 110TR and 110TL which act as camming surfaces tending to bias each leg away from the other thereby tending to cross the legs in the manner shown. This structure also prevents interference of the legs when folded toward each other.

Thus, it can be seen that the particular shape of the staple as shown, promotes a unique folding pattern for the legs which achieves the configuration shown in the bent staples of FIGS. 22 and 24. Note in particular that inwardly bent central portion 110c promotes positive attachment of the mesh to the tissue by providing a gripping system between inwardly projecting bight portion 110c and leg members 110R and 110L with mesh and tissue gripped therebetween. This staple shape combines with the arrangement of the anvils and the particularly configured pusher plate 104 to cause the staple to pierce mesh and body tissue up to a predetermined extent. At this point, continued application of force to the staple causes the staple legs to fold upon themselves as shown in the drawings while encompassing a sufficient portion of the mesh to attach the mesh to the body tissue. Thus the staple pieces folds and grips in substantially a single movement.

In practice, the laparoscopic procedures to repair tissue in hernia repair using surgical mesh is similar in some respects to the surgical procedures to gall bladders, appendix, lungs, etc. In particular, the endoscopic tubular section of the apparatus is inserted into the cannula which is positioned within the opening in the body. Provision is made between the cannula and the endoscopic section to seal the connection therebetween and provision may also be provided to seal the actual endoscopic apparatus from leakage of fluids or insufflating gaseous media. An exemplary cannula assembly including seal means is disclosed for example in commonly assigned U.S. Pat. No. 4,943,280, issued Jul. 24, 1990, the disclosure of which is incorporated herein by reference.

The Kit

The present invention is readily adaptable to be provided to surgeons in the form of a kit in which all necessary equipment and accessories are provided in sterile form ready for use in surgery. For example, an apparatus constructed according to the invention can be readily packaged with a supply of staples (i.e. up to 12 or more staples) and sufficient mesh material for completing the hernial repair. The mesh material is typically about 1 mm in thickness. The components may be provided separately as a matched kit, or in a blister type or other package, suitable and ready for use by the surgeon and the surgeon's assistants. The apparatus and staples can be provided in any size matched to meet the apparatus and mesh material in accordance with the particular needs of a contemplated hernial surgical procedure. In addition, the kit can include a matching trocar assembly with appropriate valve assembly to prevent loss of the insufflating gas from the peritoneum between the trocar and the outside surface of the endoscopic section. Since the outer housing of the endoscopic section is substantially closed at the point of attachment of the staple magazine, release of insufflating gases through the staple magazine and the endoscopic section housing is either non existent or minimal. Such trocar assembly is available from United States Surgical Corporation, Norwalk, Conn., under the trademark SURGIPORT brand trocar assembly.

A typical endoscopic section may be a 12 mm diameter with a staple magazine capable of holding up to 10 staples of appropriate size. The length of the endoscopic section is typically 14 to 15 inches. An endoscopic section in the embodiment shown will be about 14 inches. However, if pivotal movement of the staple storage magazine is to be provided between plus 45 degrees and minus 45 degrees solely by distal and proximal movement of collar 22, the endoscopic section will be structured to greater in length, i.e. about 15 inches. The trocar assembly will be of matching size, i.e., 12 mm, to accommodate the endoscopic section and to prevent release of gases thereby. The mesh material provided with the kit will be of mesh size comparable for use with the size of the staples provided in the kit.

Thus by structuring the apparatus to provide such sealing, the endoscopic application of staples to attach objects such as surgical mesh to body tissue can be readily accomplished. Accordingly, the present invention is not only directed to the apparatus for applying such staples to body tissue, but also to a kit in which the apparatus is uniquely combined with a supply of staples, surgical mesh, cannula assembly etc. whereby the surgeon may readily perform the necessary procedures.

An Alternative Embodiment

In the following description of an alternative embodiment of the invention, like components will be identified by numerals similar to the numerals for like components in the previous embodiments except that they will be preceded by the numeral "2". Accordingly, for example, the entire apparatus of the previous embodiment was identified in the description as numeral "10". In FIG. 30, for example, the apparatus is identified by numeral "210".

Figure 33:
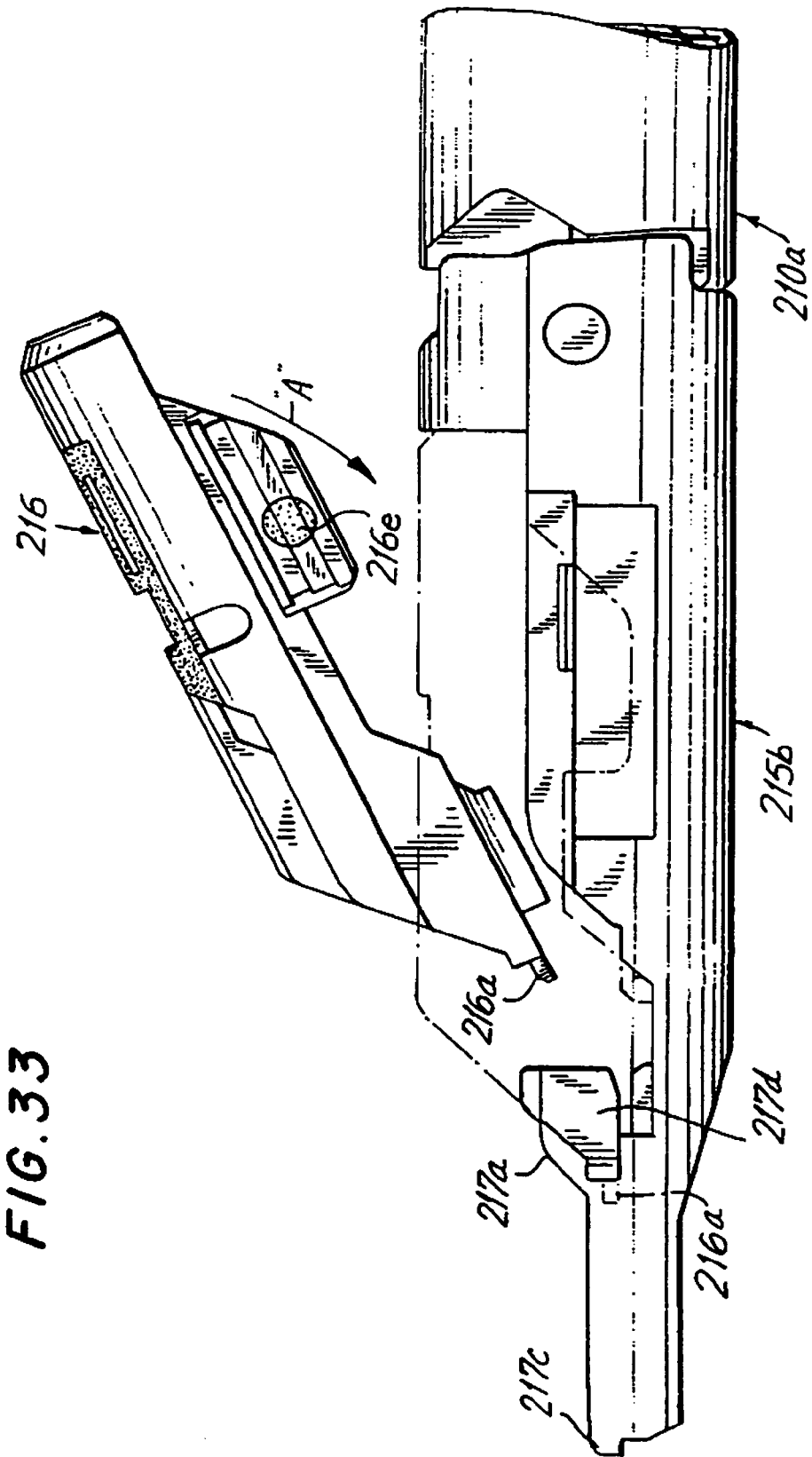
FIG. 33 is a side elevational view of the distal portion of the endoscopic section illustrating the staple storage cartridge support member and the staple storage cartridge in position for insertion onto the support member.
Figure 37:
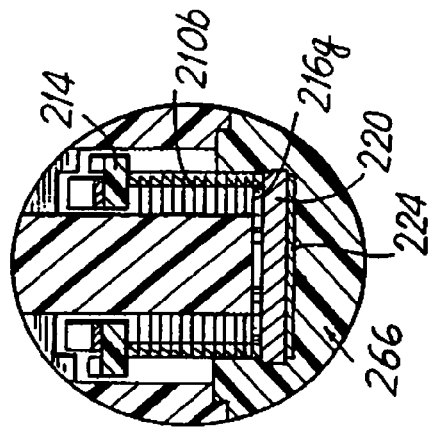
FIG. 37 is a cross-sectional view taken along lines 37-37 of FIG. 35 illustrating the staples stacked within the cartridge.

Referring now to FIG. 30, there is illustrated a perspective view of an alternative embodiment of the apparatus constructed according to the invention in which the staples are stored in a cartridge which is self-contained and which is readily insertable at the distal portion of the endoscopic section of the apparatus as shown in FIG. 33. The apparatus 210 includes handle portion 212 and endoscopic section 214 having at the distal end portion a staple storage cartridge support means 266 on which is supported staple storage cartridge 216. Generally, it may be stated that the staple cartridge support member 266 is pivotally mounted to the distal portion of the endoscopic section and such pivotal motion will result in similar pivotal motion of the staple storage cartridge 216 since the cartridge is directly supported by the pivotal support member. The pivotal motion of the staple storage cartridge support member and related mechanism is identical to the mechanism described previously in connection with the first embodiment.

Referring now to FIG. 31 the components which form the handle 212 are shown and are in many respects identical to the components and function of the handle shown in FIG. 2. The handle components shown in FIG. 31, however include an additional feature which provides a manual tactile feel to assist the user in knowing when the staple is at a particular visible position shown in FIG. 39. One way this can be achieved is shown in FIG. 31 whereby arcuately shaped notch 233 is incorporated into the triangular member 234 and is configured and dimensioned similar to the pin 236. When trigger 220 is manually squeezed by the user toward upright member 235 causing horizontal pin 236 to traverse an upward arc as described in connection with the previous embodiment the pin 236 engages the longer side 234a of triangular member 234. Thus, each time the trigger 220 is squeezed a sufficient distance, the pin 236 will enter arcuately shaped notch 233 so as to provide the user with an actual indication by feel of the location of the pin with respect to the longer side 234a of triangular member 234. At this point along the path of pin 236 the staple 210, next in line, will be at the same partially advanced distal location which is shown in FIG. 39. Thus, when the user senses or feels the detent of the entry of pin 236 into notch 233 an actual perceptible tactile indicator of the position of the staple next in line is thus provided. This partially advanced position of the staple facilitates visual examination of the staple to assist the user in selecting the proper position or location and/or orientation which would be appropriate for the particular staple application which is in progress. At all times, however, while trigger 220 is being squeezed, the uni-motion clutch mechanism 200 will prevent retracement of the trigger until the full stroke has been completed, as described previously. It should be noted that other means, including visible and audible, can be utilized to achieve the advantageous provision of indicating to the user when the staple is in its partially advanced position.

Referring now to FIGS. 32 and 32A, the unique replaceable staple cartridge system constructed according to the present invention is disclosed. In contrast to the embodiment described hereinabove the staple storage magazine and pivoting system has been replaced by the combination of a replaceable staple storage cartridge 216 shown with parts separated in FIG. 32A and a pivotal staple cartridge support system 215 shown with parts separated in FIG. 32. In summary, the pivotal staple cartridge support system is permanently attached for pivotal movement via pins 289 with respect to the endoscopic section 210 and the cartridge 216 is readily insertable with respect to the support system as shown in FIG. 33.

Referring once again to FIG. 32 the staple cartridge support system includes support member 266 having proximal upper face member 215 permanently attached thereto by ultrasonic welding, gluing etc. The entire assembly is attached for pivotal movement to endoscopic section 210 via pins 289. As described in the previous embodiment the pivotal movement of the staple cartridge support member 266 and related components is capable of extending up to about 45° with respect to the central axis of the endoscopic section 210. However, as noted previously this cartridge support system may be arranged to pivot from about +45° to about −45° by dimensioning the pivoting system appropriately.

The pivotal movement of the staple cartridge support system shown in FIG. 32 is identical in all respects to the pivotal movement of the staple storage magazine described in connection with the previous embodiment and shown particularly in FIG. 15. However, in the staple cartridge support system in FIG. 32 the structure has been modified as shown to accommodate the removable and replaceable staple cartridge 216. For example, at the distal end portion of the staple cartridge support system there is shown cartridge support plate 217 which includes a lip 217a at the proximal end for reception of the distal tips 216a of the cartridge housing to retain the cartridge 216 in position on the support member 266. In addition cartridge support plate 217 includes distally extending leg members 217b which in turn include tip portions 217c which extend distally of the tip of cartridge support member 266 as shown more clearly in FIG. 33. The tip members 217c extend not only distally but also inwardly as shown clearly in FIGS. 32 and 34 so as to provide an increased staple contact surface and backing support for each staple as it is advanced distally and as it is deformed. This feature prevents the staple from curling rearwardly as it is being deformed in the event such tendency may be present. Thus, this feature provides resistance to backward roll for each staple.

Referring once again to FIG. 32a and FIG. 32b the cartridge 216 is shown and is assembled to contain a plurality of staples which are preloaded and a spring 213 having distally extending legs 213a adapted to bias staples 210 in a direction toward the anvil 220 via staple follower 214 constructed of a suitable material such as nylon. The staples are contained in cartridge 216 by "L" shaped holders 216g on the lower face of the cartridge 216 as shown in FIG. 32B. In the present embodiment, the staple follower 214 is similar to staple follower 114 of the previous embodiment but contains a proximally extending extension 214a terminating in head 214b which extends into the space 213b defined by the legs 213a of spring 213.

Figure 36:
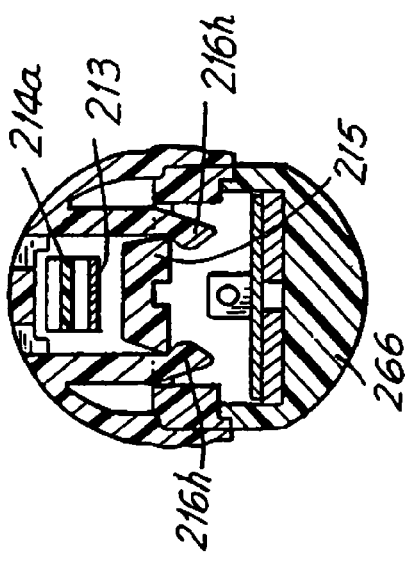
FIG. 36 is a cross-sectional view taken along lines 36-36 of FIG. 35 illustrating the initial position of the staple indicator when the cartridge is loaded with a full complement of staples.

The cartridge 216 is inserted into position as shown in FIG. 33 and is retained by positioning distal tips 216a into respective spaces 217e formed on each side between face member 215 and cartridge support member 266. Central partition 217d becomes positioned within the space 216k between cartridge distal legs 216L to stabilize the cartridge in position. Downwardly extending cartridge legs 216h shown more clearly in FIGS. 34, 35 and 36 are configured as shown, to resiliently snap into elongated apertures 215a in face member 215 as shown in FIG. 36 to retain the cartridge in position when it is rotated thereinto in the direction of arrow A as shown in FIG. 33. Thus, it is preferable to fabricate the housing of cartridge 216 of a resilient plastic material.

Figure 38:
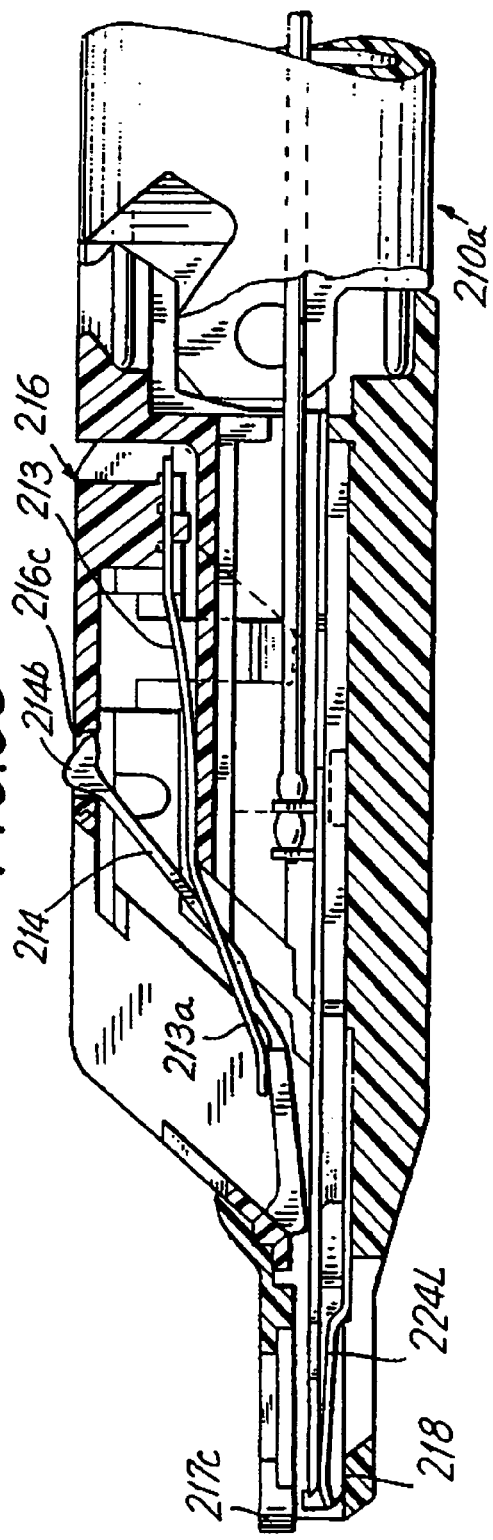
FIG. 38 is a cross-sectional view of the staple storage cartridge and related support member after the last staple has been fired.

The operation of the staple follower 214 is clearly illustrated in FIGS. 35 through 38. In FIG. 35, the staple cartridge 216 is shown with a full complement of staples 210 and the proximal portion 214a of staple follower 24 is shown extending upwardly through the legs 213a of spring 213. A window 216c is provided in the upper housing 216b of cartridge 216 to facilitate visibility of the staple follower when all staples have been spent and the proximal head 214b of staple follower 214 moves upwardly into the window 216b as shown in FIG. 38, by the action of spring 213. Thus, the user is provided with an immediate visible indicator when all staples have been spent.

In addition, it is desirable to fabricate staple follower 214 of a bright colored plastic material such as nylon. For example, follower 214 could be fabricated of a bright yellow material at least at the head 214b such that a visible indication will be provided by head 214b after the last staple has been spent. In assembled condition, the head 214b and extension 214a will be positioned in space 213b between legs 213a of spring 213 as shown in FIGS. 35 and 38. In addition, it is desirable to color the area 216d of upper housing 216b of the cartridge 216 in a color similar to the color of the extension 214a of follower 214. For example, follower 214 may be colored black in its entirety with the exception of head 214b which would be colored bright yellow.

The area 216d of the upper housing 216b (shown by the stippled portions in FIGS. 32A and 34) can also be colored black. Thus, when a full complement of staples 210 is provided as in FIG. 35, the black portion of extension 214a of follower 214 will appear through window 216c and this black color will complement the black colored area 216d shown by stippling in FIG. 34. Follower 214 is fabricated of a resilient material such as nylon and is configured to be upwardly biased against the inner ceiling 216j as the staples are individually dispensed. When the last staple has been dispensed and closed as shown in FIG. 38, the yellow colored head 214b of follow 213 will snap upwardly under its own resilience to thereby appear through window 216c and the user will therefore be provided with an immediate visible indication that the last staple has been spent. Thereafter, the cartridge may be simply removed by lifting it away from the pivotal support member 266 in the direction opposite the direction shown by the arrow A shown in FIG. 33. The cartridge may be replaced by a fully loaded cartridge and the surgical operation may proceed.

Another feature of the cartridge of the present invention is the provision of colored circular dots 216e and 216f. One of each such circular dot is shown on upper cartridge housing 216b by circles surrounded by stippled areas in FIGS. 32A and 33. By placing the user's thumb and first middle finger on the two dots 216e on each side of the upper housing 216b, and the index finger on the forward dot 216f, the cartridge may be simply lifted from the pivotal support member 266 causing cartridge legs 216h to release their snap grip on face member 215. Thereafter, a full cartridge may be replaced in the same, but reverse fashion by positioning tips 216a into space 217e and snapping legs 216h into position with apertures 215a. The circular dots 216e and 216f can be provided in any suitable color which is readily observable to the user. For example, these circular dots may be provided in the color black, which would be readily visible in contrast to the yellow indicator of head 214b of staple follower 214.

Figure 13:
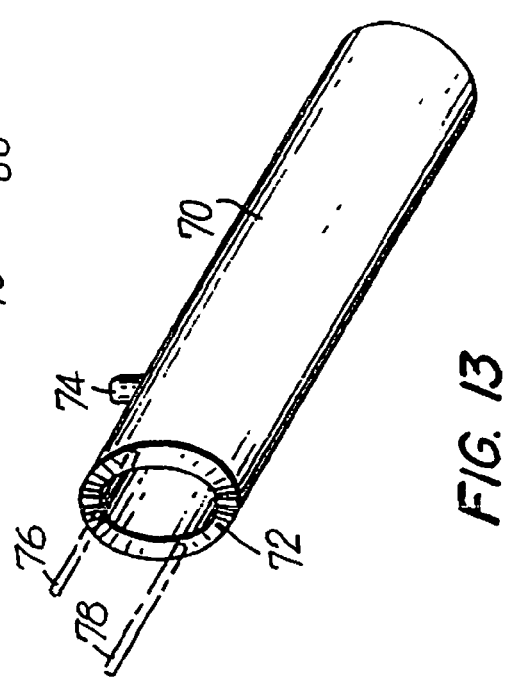
FIG. 13 is a perspective view of an internal sleeve and pin which coacts with the inner sleeve shown in FIGS. 11 and 12 which forms part of the system for pivoting the staple magazine at the distal end.

Referring now to FIG. 40, there is illustrated a circular sleeve 270 similar to the circular sleeve 70 shown in FIG. 13 in connection with the previous embodiment. The circular sleeve 270 is identical in all respects to the cylindrical sleeve 270 of the previous embodiment and is configured as a camming surface adapted to engage push rods 276, 278 to pivot the cartridge support member 266 and the staple cartridge 216 in the same manner as described in connection with the previous embodiment. In FIG. 40 grooves 270a and 270b are illustrated to provide a positive stop which corresponds to the engagement of push rod 276, 278 with grooves 270a and 270b when the staple storage cartridge support system 266 is in the pivotal position, i.e. approximately 45° with respect to the endoscopic section. The positive stop which is provided by the engagement of the push rods 276, 278 with the grooves 270a and 270b is identical to the operation of sleeve 70 described in connection with the previous embodiment. However, optionally additional grooves 270c and 270d may be provided in sleeve 270 corresponding to pivotal locations of the cartridge support member 266 which are less than the full pivotal movement of the support system, i.e. 25°. These optional grooves will facilitate providing a perceptible tactile indication to the user of the location of the cartridge and related support system in terms of pivotal angle with respect to the endoscopic section. Optionally any number of such grooves may be provided dependent upon the particular needs of the user and the particular surgical procedures required. Thus, the instrument may be provided with any number of combinations of the above-described features.

FIG. 41 is a cross-sectional view taken along lines 41-41 of FIG. 30, illustrating schematically a gaseous seal means in the form of silicone grease 250 to prevent the insufflating gaseous media from escaping from the patient's body cavity through the instrument. Such gaseous seal means may alternatively be in the form of a separate seal block positioned within the endoscopic section, or it may alternatively be in the form of a gaseous sealing block located either in another portion of the endoscopic section or alternatively in the handle section.

The present embodiment may be incorporated into kit form as in the previously described embodiment. Also, combinations of features of the present embodiment may be combined with features described in connection with the previous embodiment as may become apparent to persons skilled in the art.

What is claimed is:

1. A surgical instrument comprising:
an elongate member defining a longitudinal axis; an end effector pivotably coupled to a distal end of the elongate member; and an articulation mechanism operably coupled to the end effector, the articulation mechanism including:
a collar movably mounted on the elongate member, and first and second rods operatively coupling the collar to the end effector such that axial movement of the collar along the longitudinal axis urges the first rod in a proximal direction and the second rod in a distal direction, thereby pivoting the end effector relative to a longitudinal axis of the elongate member.

2. The surgical instrument of claim 1, wherein the end effector is pivotable throughout a plurality of positions relative to the longitudinal axis of the elongate member.

3. The surgical instrument of claim 1, wherein the collar is movable along the elongate member from a first position to a second position.

4. The surgical instrument of claim 1, further including a cartridge having at least one fastener, the cartridge being removably attached to the end effector.

5. The surgical instrument of claim 4, wherein the end effector is pivotable throughout a plurality of positions including a first position that is aligned with the longitudinal axis and a second position that is axially offset from the longitudinal axis.

6. The surgical instrument of claim 5, wherein the at least one fastener is longitudinally translatable through the cartridge in each position of the plurality of positions.

7. The surgical instrument of claim 1, wherein the articulation mechanism further includes a first sleeve disposed within the collar for concomitant rotation with the collar, the first sleeve defining a helical groove, and a second sleeve disposed within the first sleeve, the second sleeve having a pin extending radially outward, the pin configured for slidable movement within the helical groove of the first sleeve such that the longitudinal movement of the collar causes the pin to follow the groove causing the second sleeve to rotate in one direction.

8. The surgical instrument of claim 7, wherein the second sleeve includes a obliquely oriented distal face, the face engaging proximal ends of the first and second rods, such that when the collar is moved longitudinally, the second sleeve rotates causing the first and second rods to move in opposite directions.

* * * * *